US007119176B2

(12) United States Patent
Tanabe et al.

(10) Patent No.: US 7,119,176 B2
(45) Date of Patent: Oct. 10, 2006

(54) ANTIBODIES SPECIFIC TO HUMAN PROSTACYCLIN SYNTHASE

(76) Inventors: Tadashi Tanabe, 18-13, Higashitoyonaka-cho 3-chome, Toyonaka-shi, Osaka 560-0003 (JP); Chieko Yokoyama, 39-1-303, Nakajuku, Itabashi-ku, Tokyo 173-0005 (JP)

( * ) Notice: Subject to any disclaimer, the term of this patent is extended or adjusted under 35 U.S.C. 154(b) by 208 days.

(21) Appl. No.: 10/663,749

(22) Filed: Sep. 17, 2003

(65) Prior Publication Data
US 2004/0092722 A1    May 13, 2004

Related U.S. Application Data

(60) Continuation-in-part of application No. 10/608,536, filed on Jun. 30, 2003, which is a continuation of application No. 09/670,582, filed on Sep. 27, 2000, now abandoned, which is a continuation of application No. 09/037,758, filed on Mar. 10, 1998, now abandoned, which is a division of application No. 08/578,709, filed on Dec. 28, 1995, now Pat. No. 5,814,509.

(30) Foreign Application Priority Data
Apr. 28, 1994   (JP)   .................. 6-114316

(51) Int. Cl.
C07K 16/00    (2006.01)
(52) U.S. Cl. ................. 530/388.15; 530/387.9
(58) Field of Classification Search ........... 530/388.15, 530/387.9
See application file for complete search history.

(56) References Cited

OTHER PUBLICATIONS

Colman, Research in Immunology, 1994, 145(1):33-36.*
Miyata et al. Biochem. Biophy. Res. Comm. 1994, 200(30):1728-1734.*
Campbell, 1984, Monoclonal Antibody Technology, Elsevier Sc. Publishers, p. 1-32.*
Kuby, Immunology, p. 14-15, W.H. Freeman Co. 4th Ed.,2000.*
Babette B. Weksler; Heparin and Acidic Fibroblast Growth Factor Interact to Decrease Prostacyclin Synthesis in Human Endothelial Cells by Affecting Both Prostaglandin H Synthase and Prostacyclin Synthase; J. Cell. Physiol., 142[3], p. 514-522, 1990.
Ngo et al. (1994) Computational Complexity, Protein Structure Prediction, and the Levinthal Paradox. In: The Protein Folding Proble and Tertiary Structure Prediction, Eds. Merz et al., Birkhauser, Boston, MA pp. 491-495.
Weksler, Heparin and Acidic Fibroblast Growth Factor Interact to Decrease Prostacyclin Synthesis in Human Endothelial Cells by Affecting Both Prostaglandin H Synthase and Prostacyclin Synthase; *J. Cell. Physiol.*, 142(3):514-522 (1990).
Hara et al., Isolation and Molecular Cloning of Prostacyclin Synthase from Bovine Endothelial Cells,*J. Biol. Chem.* 269:19897-19903 (1994).

Smith et al., Bimodal Distribution of the Prostaglandin $I_2$ Synthase Antigen in Smooth Muscle Cells, *J. Biol. Chem.*, 258(9):5922-5926 (1983).
Smith et al., Purification, Quantitation, and Localization of $PGI_2$ Synthase Using Monoclonal Antibodies, *Adv Prostaglandin Thromboxane Leukot Res.* 11:87-92 (1983).
S. Moncada, Eighth Gaddum Memorial Lecture. University of London Institute of Education, Dec. 1980. Biological importance of prostacyclin. *Br J Pharmacol.* 76(1):3-31 (1982).
Gorman et al., Agonist-Specific Desensitization of $PGI_2$-Stimulated Cyclic AMP Accumulation by $PGE_1$ In Human Foreskin Fibroblasts, *Prostaglandins*, 19(1):2-16 (1980).
Cytochrome P-450, Biochemistry, Biophysics and Environmental Implications, Proceedings of the 4th International Conference on Cytochrome P-450 held in Kuopio, Finland, May 31-Jun. 3, 1992, E. Hietanen et al., eds., pp. 103-106, 1982.
DeWitt et al., Purification of Prostacyclin Synthase from Bovine Aorta By Immunoaffinity Chromatography, *J. Biol. Chem.*, 258(5):3285-93 (1983).
M. Inoue, Molecular Characterization of the Prostacyclin Synthase, *Adv Prostaglandin Thromboxane Leukot Res.* 17A:29-33 (1987).
Pereira et al., Bovine Prostacyclin Synthase: Purification and Isolation of Partial cDNA, *Biochem. Biophys. Res. Comm.* 197(3):1041-1048 (1993).
T. Shimizu, Structure-function relationships of membrane-bound heme-enzyme, cytochrome P450, Institute for Chemical Reaction Science, Tohoku University, pp. 10-15, 1992.
Salmon et al., Preparation and Assay of Prostacyclin Synthase, Methods in Enzymology, 86:91-99 (1982).
Tanabe et al., Molecular Cloning of Prostacyclin Synthase From Bovine Endothelial Cells, in Eicosandoids & Other BioActive Lipids in Cancer, Inflammation and Radiation Injury, 3rd Int'l Conf., Georgetown Conference Center, Washington D.C., pp. 137, Oct. 13-16, 1993.
Tanabe et al., Advances in Prostaglandin, Thromboxany and Leukotriene Research, vol. 23, 1995, pp. 133-135.
Govindarajan et al, Immunohistochemical distribution of renal prostaglandin endoperoxide synthase and prostacyclin synthase: diminished endoperoxide synthase in the hepatorenal syndrome. *Hepatology* 7(4):654-659 (1987).

(Continued)

*Primary Examiner*—Christina Chan
*Assistant Examiner*—Yunsoo Kim
(74) *Attorney, Agent, or Firm*—Sughrue Mion, PLLC

(57) ABSTRACT

The present invention clarifies the primary structure of human-originated PGIS and the nucleotide sequence encoding same. The PGIS and its DNA are useful as reagents for the development of therapeutic agents for the cardiovascular diseases induced by the production imbalance between $PGI_2$ and $TXA_2$, and as diagnostics for determining the in vivo tissue expression level and distribution of PGIS or mRNA thereof. Moreover, they can be used as therapeutic agents for cardiovascular diseases, which introduce PGIS and the like into human or other animals in a lesion-specific manner. The production method of the present invention is useful for the easy and efficient mass production of the human-originated PGIS. The antibody of the present invention is useful for the purification of the human-originated PGIS and immunohistochemical analysis of the cause of a disease.

16 Claims, 14 Drawing Sheets

OTHER PUBLICATIONS

Keirse et al., Does or can human placenta produce prostacyclin? *Placenta* 7(1):37-42 (1986).

Siegle et al, Characterization of monoclonal antibodies generated against bovine and porcine prostacyclin synthase and quantitation of bovine prostacyclin synthase, *FEBS lett.* 347(2-3):221-5 (1994).

Dewitt et al., Monoclonal antibodies against PG12 synthase: an immunoradiometric assay for quantitating the enzyme. *Methods Enzymol.* 86:240-246 (1982).

Moonen et al., Immunohistochemical localisation of prostaglandin endoperoxide synthase and prostacyclin synthase in pregnant human myometrium. *Eur J Obstet Gynecol Reprod Biol.* 19(3):151-158 (1985).

Harlow et al, Antibodies a Laboratory Manual, Cold Spring Harbor Laboratories, 1989, Chap. 8, pp. 283-318.

Satoh et al., Role of prostaglandins in pregnancy-induced hypertension, *Am. J. Kidney*, 17(2):133-138 (1991).

Gryglewski et al., Prostacyclin and Vascular Disease, *Philos. Trans. R. Soc. Lond. B. Biol. Sci.*, 294(1072):383-388 (1981).

Pereira et al., Molecular Cloning and Characterization of Bovine Prostacyclin Synthase, *Biochem. Biophys. Res. Commun.* 203(1):59-65 (1994).

* cited by examiner

SEQUENCE LISTING

<160> NUMBER OF SEQ ID NOS: 20

<210> SEQ ID NO 1
<211> LENGTH: 16
<212> TYPE: DNA

```
<213> ORGANISM: Artificial Sequence
<220> FEATURE:
<223> OTHER INFORMATION: Description of Artificial Sequence: Primer

<400> SEQUENCE: 1
gggacaagga ccacat                                                        16

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
caaaagtcgc ctgtggaagc                                                    20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 3
cacaggcgac ttttgaca                                                      18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
tgcctgcatc tcctctga                                                      18

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 5
gactcgagtc gacatcgatt tttttttttt ttttt                                   35

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 6
gactcgagtc gacatcg                                                       17

<210> SEQ ID NO 7
<211> LENGTH: 48
<212> TYPE: DNA
<213> ORGANISM: Artificial Sequence
<220> FEATURE:
<223> OTHER INFORMATION: Description of Combined DNA/RNA Molecule:
      Primer
<220> FEATURE:
<223> OTHER INFORMATION: Description of Artificial Sequence: Primer
<220> FEATURE:
```

```
<221> NAME/KEY: modified_base
<222> LOCATION: (36)..(37)
<223> OTHER INFORMATION: Inosine
<220> FEATURE:
<221> NAME/KEY: modified_base
<222> LOCATION: (41)..(42)
<223> OTHER INFORMATION: Inosine
<220> FEATURE:
<221> NAME/KEY: modified_base
<222> LOCATION: (46)..(47)
<223> OTHER INFORMATION: Inosine

<400> SEQUENCE: 7
cuacuacuac uaggccacgc gucgacuagu acgggnnggg nngggnng                48

<210> SEQ ID NO 8
<211> LENGTH: 183
<212> TYPE: DNA
<213> ORGANISM: Homo sapiens
<220> FEATURE:
<221> NAME/KEY: CDS
<222> LOCATION: (1)..(183)

<400> SEQUENCE: 8 ggg gac aag gac cac atg tgc agt gtc aaa agt cgc ctg tgg aag ctg    48
Gly Asp Lys Asp His Met Cys Ser Val Lys Ser Arg Leu Trp Lys Leu
 1               5                  10                  15 cta tcc cca gcc agg ctg gcc agg cgg gcc cac cgg agc aaa tgg ctg    96
Leu Ser Pro Ala Arg Leu Ala Arg Arg Ala His Arg Ser Lys Trp Leu
             20                  25                  30 gag agt tac ctg ctg cac ctg gag gag atg ggt gtg tca gag gag atg   144
Glu Ser Tyr Leu Leu His Leu Glu Glu Met Gly Val Ser Glu Glu Met
         35                  40                  45 cag gca cgg gcc ctg gtg ctg cag ctg tgg gcc aca cag                183
Gln Ala Arg Ala Leu Val Leu Gln Leu Trp Ala Thr Gln
     50                  55                  60

<210> SEQ ID NO 9
<211> LENGTH: 61
<212> TYPE: PRT
<213> ORGANISM: Homo sapiens

<400> SEQUENCE: 9

Gly Asp Lys Asp His Met Cys Ser Val Lys Ser Arg Leu Trp Lys Leu
 1               5                  10                  15

Leu Ser Pro Ala Arg Leu Ala Arg Arg Ala His Arg Ser Lys Trp Leu
             20                  25                  30

Glu Ser Tyr Leu Leu His Leu Glu Glu Met Gly Val Ser Glu Glu Met
         35                  40                  45

Gln Ala Arg Ala Leu Val Leu Gln Leu Trp Ala Thr Gln
     50                  55                  60

<210> SEQ ID NO 10
<211> LENGTH: 792
<212> TYPE: DNA
<213> ORGANISM: Homo sapiens
<220> FEATURE:
<221> NAME/KEY: CDS
<222> LOCATION: (80)..(790)

<400> SEQUENCE: 10
ctactactac taggccacgc gtcgactagt acggggggggg ggggggggggg gcagccccgc    60 cagccccgcc agccccgcg atg gct tgg gcc gcg ctc ctc ggc ctc ctg gcc    112
                     Met Ala Trp Ala Ala Leu Leu Gly Leu Leu Ala
                      1               5                  10
```

```
gca ctg ttg ctg ctg ctg cta ctg agc cgc cgc acg cgg cga cct      160
Ala Leu Leu Leu Leu Leu Leu Leu Ser Arg Arg Arg Thr Arg Arg Pro
         15                  20                  25 ggt gag cct ccc ctg gac ctg ggc agc atc ccc tgg ttg ggg tat gcc  208
Gly Glu Pro Pro Leu Asp Leu Gly Ser Ile Pro Trp Leu Gly Tyr Ala
         30                  35                  40 ttg gac ttt gga aaa gat gct gcc agc ttc ctc acg agg atg aag gag  256
Leu Asp Phe Gly Lys Asp Ala Ala Ser Phe Leu Thr Arg Met Lys Glu
     45                  50                  55 aag cac ggt gac atc ttt act ata ctg gtt ggg ggc agg tat gtc acc  304
Lys His Gly Asp Ile Phe Thr Ile Leu Val Gly Gly Arg Tyr Val Thr
 60                  65                  70                  75 gtt ctc ctg gac cca cac tcc tac gac gcg gtg gtg tgg gag cct cgc  352
Val Leu Leu Asp Pro His Ser Tyr Asp Ala Val Val Trp Glu Pro Arg
                 80                  85                  90 acc agg ctc gac ttc cat gcc tat gcc atc ttc ctc atg gag agg att  400
Thr Arg Leu Asp Phe His Ala Tyr Ala Ile Phe Leu Met Glu Arg Ile
             95                 100                 105 ttt gat gtg cag ctt cca cat tac agc ccc agt gat gaa aag gcc agg  448
Phe Asp Val Gln Leu Pro His Tyr Ser Pro Ser Asp Glu Lys Ala Arg
         110                 115                 120 atg aaa ctg act ctt ctc cac aga gag ctc cag gca ctc aca gaa gcc  496
Met Lys Leu Thr Leu Leu His Arg Glu Leu Gln Ala Leu Thr Glu Ala
     125                 130                 135 atg tat acc aac ctc cat gca gtg ctg ttg ggc gat gct aca gaa gca  544
Met Tyr Thr Asn Leu His Ala Val Leu Leu Gly Asp Ala Thr Glu Ala
140                 145                 150                 155 ggc agt ggc tgg cac gag atg ggt ctc ctc gac ttc tcc tac agc ttc  592
Gly Ser Gly Trp His Glu Met Gly Leu Leu Asp Phe Ser Tyr Ser Phe
                 160                 165                 170 ctg ctc aga gcc ggc tac ctg act ctt tac gga att gag gcg ctg cca  640
Leu Leu Arg Ala Gly Tyr Leu Thr Leu Tyr Gly Ile Glu Ala Leu Pro
             175                 180                 185 cgc acc cat gaa agc cag gcc cag gac cgc gtc cac tca gct gat gtc  688
Arg Thr His Glu Ser Gln Ala Gln Asp Arg Val His Ser Ala Asp Val
         190                 195                 200 ttc cac acc ttt cgc cag ctc gac cgg ctg ctc ccc aaa ctg gcc cgt  736
Phe His Thr Phe Arg Gln Leu Asp Arg Leu Leu Pro Lys Leu Ala Arg
     205                 210                 215 ggc tcc ctg tca gtg ggg gac aag gac cac atg tgc agt gtc aaa agt  784
Gly Ser Leu Ser Val Gly Asp Lys Asp His Met Cys Ser Val Lys Ser
220                 225                 230                 235 cgc ctg tg                                                        792
Arg Leu
```

<210> SEQ ID NO 11
<211> LENGTH: 237
<212> TYPE: PRT
<213> ORGANISM: Homo sapiens

<400> SEQUENCE: 11

```
Met Ala Trp Ala Ala Leu Leu Gly Leu Leu Ala Leu Leu Leu Leu
 1               5                  10                  15

Leu Leu Leu Ser Arg Arg Arg Thr Arg Arg Pro Gly Glu Pro Pro Leu
             20                  25                  30

Asp Leu Gly Ser Ile Pro Trp Leu Gly Tyr Ala Leu Asp Phe Gly Lys
         35                  40                  45

Asp Ala Ala Ser Phe Leu Thr Arg Met Lys Glu Lys His Gly Asp Ile
     50                  55                  60
```

```
Phe Thr Ile Leu Val Gly Gly Arg Tyr Val Thr Val Leu Leu Asp Pro
 65                  70                  75                  80

His Ser Tyr Asp Ala Val Val Trp Glu Pro Arg Thr Arg Leu Asp Phe
             85                  90                  95

His Ala Tyr Ala Ile Phe Leu Met Glu Arg Ile Phe Asp Val Gln Leu
            100                 105                 110

Pro His Tyr Ser Pro Ser Asp Glu Lys Ala Arg Met Lys Leu Thr Leu
        115                 120                 125

Leu His Arg Glu Leu Gln Ala Leu Thr Glu Ala Met Tyr Thr Asn Leu
    130                 135                 140

His Ala Val Leu Leu Gly Asp Ala Thr Glu Ala Gly Ser Gly Trp His
145                 150                 155                 160

Glu Met Gly Leu Leu Asp Phe Ser Tyr Ser Phe Leu Leu Arg Ala Gly
                165                 170                 175

Tyr Leu Thr Leu Tyr Gly Ile Glu Ala Leu Pro Arg Thr His Glu Ser
            180                 185                 190

Gln Ala Gln Asp Arg Val His Ser Ala Asp Val Phe His Thr Phe Arg
        195                 200                 205

Gln Leu Asp Arg Leu Leu Pro Lys Leu Ala Arg Gly Ser Leu Ser Val
    210                 215                 220

Gly Asp Lys Asp His Met Cys Ser Val Lys Ser Arg Leu
225                 230                 235

<210> SEQ ID NO 12
<211> LENGTH: 1296
<212> TYPE: DNA
<213> ORGANISM: Homo sapiens
<220> FEATURE:
<221> NAME/KEY: CDS
<222> LOCATION: (3)..(827)

<400> SEQUENCE: 12 gg gac aag gac cac atg tgc agt gtc aaa agt cgc ctg tgg aag ctg      47
   Asp Lys Asp His Met Cys Ser Val Lys Ser Arg Leu Trp Lys Leu
    1               5                  10                  15 cta tcc cca gcc agg ctg gcc agg cgg gcc cac cgg agc aaa tgg ctg     95
Leu Ser Pro Ala Arg Leu Ala Arg Arg Ala His Arg Ser Lys Trp Leu
            20                  25                  30 gag agt tac ctg ctg cac ctg gag gag atg ggt gtg tca gag gag atg    143
Glu Ser Tyr Leu Leu His Leu Glu Glu Met Gly Val Ser Glu Glu Met
        35                  40                  45 cag gca cgg gcc ctg gtg ctg cag ctg tgg gcc aca cag ggg aat atg    191
Gln Ala Arg Ala Leu Val Leu Gln Leu Trp Ala Thr Gln Gly Asn Met
    50                  55                  60 ggt ccc gct gcc ttc tgg ctc ctg ctc ttc ctt ctc aag aat cct gaa    239
Gly Pro Ala Ala Phe Trp Leu Leu Leu Phe Leu Leu Lys Asn Pro Glu
 65                  70                  75 gcc ctg gct gct gtc cgc gga gag ctc gag agt atc ctt tgg caa gcg    287
Ala Leu Ala Ala Val Arg Gly Glu Leu Glu Ser Ile Leu Trp Gln Ala
 80                  85                  90                  95 gag cag cct gtc tcg cag acg acc act ctc cca cag aag gtt cta gac    335
Glu Gln Pro Val Ser Gln Thr Thr Thr Leu Pro Gln Lys Val Leu Asp
                100                 105                 110 agc aca cct gtg ctt gat agc gtg ctg agt gag agc ctc agg ctt aca    383
Ser Thr Pro Val Leu Asp Ser Val Leu Ser Glu Ser Leu Arg Leu Thr
            115                 120                 125 gct gcc ccc ttc atc acc cgc gag gtt gtg gtg gac ctg gcc atg ccc    431
Ala Ala Pro Phe Ile Thr Arg Glu Val Val Val Asp Leu Ala Met Pro
```

-continued

```
                     130                 135                 140
atg gca gac ggg aga gaa ttc aac ctg cga cgt ggt gac cgc ctc ctc      479
Met Ala Asp Gly Arg Glu Phe Asn Leu Arg Arg Gly Asp Arg Leu Leu
    145                 150                 155 ctc ttc ccc ttc ctg agc ccc cag aga gac cca gaa atc tac aca gac      527
Leu Phe Pro Phe Leu Ser Pro Gln Arg Asp Pro Glu Ile Tyr Thr Asp
160                 165                 170                 175 cca gag gta ttt aaa tac aac cga ttc ctg aac cct gac gga tca gag      575
Pro Glu Val Phe Lys Tyr Asn Arg Phe Leu Asn Pro Asp Gly Ser Glu
                180                 185                 190 aag aaa gac ttt tac aag gat ggg aaa cgg ctg aag aat tac aac atg      623
Lys Lys Asp Phe Tyr Lys Asp Gly Lys Arg Leu Lys Asn Tyr Asn Met
            195                 200                 205 ccc tgg ggg gcg ggg cac aat cac tgc ctg ggg agg agt tat gcg gtc      671
Pro Trp Gly Ala Gly His Asn His Cys Leu Gly Arg Ser Tyr Ala Val
        210                 215                 220 aac agc atc aaa caa ttt gtg ttc ctt gtg ctg gtg cac ttg gac ttg      719
Asn Ser Ile Lys Gln Phe Val Phe Leu Val Leu Val His Leu Asp Leu
    225                 230                 235 gag ctg atc aac gca gat gtg gag atc cct gag ttt gac ctc agc agg      767
Glu Leu Ile Asn Ala Asp Val Glu Ile Pro Glu Phe Asp Leu Ser Arg
240                 245                 250                 255 tac ggc ttc ggt ctg atg cag ccg gaa cac gac gtg ccc gtc cgc tac      815
Tyr Gly Phe Gly Leu Met Gln Pro Glu His Asp Val Pro Val Arg Tyr
                260                 265                 270 cgc atc cgc cca tgacacaggg agcagatgga tccacgtgct cgcctctgcc         867
Arg Ile Arg Pro
            275 cagcctgccc cagcctgccc cagcctccca gctttctgtg tgcacagttg gcccgggtgc    927 aggtgctagc attaccactt ccctgctttt ctcccagaag gctgggtcca ggggagggaa    987 aagctaagag ggtgaacaaa gaaaagacat gaaagctct atggattatc cactgcaaag     1047 ttttctttcc aaaatcaggc tttgtctgct cccaattcac ctcgttactc tcacctcgtg    1107 atatccacaa atgctattca gataaggcag aactaggagt cttcactgct ctgcccccaa    1167 ctcccggagg tgtcaccttc ctagttctta tgagctagca tggcccgggc cttatccagt    1227 caaagcggat gctggccaca gaaaggccac tcaggatgtc ctttgtgtcc atcgatgtcg    1287 actcgagtc                                                            1296
```

<210> SEQ ID NO 13
<211> LENGTH: 275
<212> TYPE: PRT
<213> ORGANISM: Homo sapiens

<400> SEQUENCE: 13

```
Asp Lys Asp His Met Cys Ser Val Lys Ser Arg Leu Trp Lys Leu Leu
 1               5                  10                  15

Ser Pro Ala Arg Leu Ala Arg Arg Ala His Arg Ser Lys Trp Leu Glu
            20                  25                  30

Ser Tyr Leu Leu His Leu Glu Glu Met Gly Val Ser Glu Glu Met Gln
        35                  40                  45

Ala Arg Ala Leu Val Leu Gln Leu Trp Ala Thr Gln Gly Asn Met Gly
    50                  55                  60

Pro Ala Ala Phe Trp Leu Leu Phe Leu Leu Lys Asn Pro Glu Ala
65                  70                  75                  80

Leu Ala Ala Val Arg Gly Glu Leu Glu Ser Ile Leu Trp Gln Ala Glu
                85                  90                  95
```

```
Gln Pro Val Ser Gln Thr Thr Thr Leu Pro Gln Lys Val Leu Asp Ser
                100                 105                 110

Thr Pro Val Leu Asp Ser Val Leu Ser Glu Ser Leu Arg Leu Thr Ala
            115                 120                 125

Ala Pro Phe Ile Thr Arg Glu Val Val Asp Leu Ala Met Pro Met
130                 135                 140

Ala Asp Gly Arg Glu Phe Asn Leu Arg Arg Gly Asp Arg Leu Leu Leu
145                 150                 155                 160

Phe Pro Phe Leu Ser Pro Gln Arg Asp Pro Glu Ile Tyr Thr Asp Pro
                165                 170                 175

Glu Val Phe Lys Tyr Asn Arg Phe Leu Asn Pro Asp Gly Ser Glu Lys
            180                 185                 190

Lys Asp Phe Tyr Lys Asp Gly Lys Arg Leu Lys Asn Tyr Asn Met Pro
        195                 200                 205

Trp Gly Ala Gly His Asn His Cys Leu Gly Arg Ser Tyr Ala Val Asn
    210                 215                 220

Ser Ile Lys Gln Phe Val Phe Leu Val Leu Val His Leu Asp Leu Glu
225                 230                 235                 240

Leu Ile Asn Ala Asp Val Glu Ile Pro Glu Phe Asp Leu Ser Arg Tyr
                245                 250                 255

Gly Phe Gly Leu Met Gln Pro Glu His Asp Val Pro Val Arg Tyr Arg
            260                 265                 270

Ile Arg Pro
        275

<210> SEQ ID NO 14
<211> LENGTH: 1977
<212> TYPE: DNA
<213> ORGANISM: Homo sapiens
<220> FEATURE:
<221> NAME/KEY: CDS
<222> LOCATION: (28)..(1527)

<400> SEQUENCE: 14
agccccgcca gccccgccag ccccgcg atg gct tgg gcc gcg ctc ctc ggc ctc      54
                                Met Ala Trp Ala Ala Leu Leu Gly Leu
                                  1               5 ctg gcc gca ctg ttg ctg ctg ctg cta ctg agc cgc cgc cgc acg cgg      102
Leu Ala Ala Leu Leu Leu Leu Leu Leu Leu Ser Arg Arg Arg Thr Arg
 10                  15                  20                  25 cga cct ggt gag cct ccc ctg gac ctg ggc agc atc ccc tgg ttg ggg      150
Arg Pro Gly Glu Pro Pro Leu Asp Leu Gly Ser Ile Pro Trp Leu Gly
                 30                  35                  40 tat gcc ttg gac ttt gga aaa gat gct gcc agc ttc ctc acg agg atg      198
Tyr Ala Leu Asp Phe Gly Lys Asp Ala Ala Ser Phe Leu Thr Arg Met
             45                  50                  55 aag gag aag cac ggt gac atc ttt act ata ctg gtt ggg ggc agg tat      246
Lys Glu Lys His Gly Asp Ile Phe Thr Ile Leu Val Gly Gly Arg Tyr
         60                  65                  70 gtc acc gtt ctc ctg gac cca cac tcc tac gac gcg gtg gtg tgg gag      294
Val Thr Val Leu Leu Asp Pro His Ser Tyr Asp Ala Val Val Trp Glu
     75                  80                  85 cct cgc acc agg ctc gac ttc cat gcc tat gcc atc ttc ctc atg gag      342
Pro Arg Thr Arg Leu Asp Phe His Ala Tyr Ala Ile Phe Leu Met Glu
 90                  95                 100                 105 agg att ttt gat gtg cag ctt cca cat tac agc ccc agt gat gaa aag      390
Arg Ile Phe Asp Val Gln Leu Pro His Tyr Ser Pro Ser Asp Glu Lys
                110                 115                 120
```

-continued

```
gcc agg atg aaa ctg act ctt ctc cac aga gag ctc cag gca ctc aca    438
Ala Arg Met Lys Leu Thr Leu Leu His Arg Glu Leu Gln Ala Leu Thr
            125                 130                 135 gaa gcc atg tat acc aac ctc cat gca gtg ctg ttg ggc gat gct aca    486
Glu Ala Met Tyr Thr Asn Leu His Ala Val Leu Leu Gly Asp Ala Thr
        140                 145                 150 gaa gca ggc agt ggc tgg cac gag atg ggt ctc ctc gac ttc tcc tac    534
Glu Ala Gly Ser Gly Trp His Glu Met Gly Leu Leu Asp Phe Ser Tyr
155                 160                 165 agc ttc ctg ctc aga gcc ggc tac ctg act ctt tac gga att gag gcg    582
Ser Phe Leu Leu Arg Ala Gly Tyr Leu Thr Leu Tyr Gly Ile Glu Ala
170                 175                 180                 185 ctg cca cgc acc cat gaa agc cag gcc cag gac cgc gtc cac tca gct    630
Leu Pro Arg Thr His Glu Ser Gln Ala Gln Asp Arg Val His Ser Ala
                190                 195                 200 gat gtc ttc cac acc ttt cgc cag ctc gac cgg ctg ctc ccc aaa ctg    678
Asp Val Phe His Thr Phe Arg Gln Leu Asp Arg Leu Leu Pro Lys Leu
            205                 210                 215 gcc cgt ggc tcc ctg tca gtg ggg gac aag gac cac atg tgc agt gtc    726
Ala Arg Gly Ser Leu Ser Val Gly Asp Lys Asp His Met Cys Ser Val
        220                 225                 230 aaa agt cgc ctg tgg aag ctg cta tcc cca gcc agg ctg gcc agg cgg    774
Lys Ser Arg Leu Trp Lys Leu Leu Ser Pro Ala Arg Leu Ala Arg Arg
235                 240                 245 gcc cac cgg agc aaa tgg ctg gag agt tac ctg ctg cac ctg gag gag    822
Ala His Arg Ser Lys Trp Leu Glu Ser Tyr Leu Leu His Leu Glu Glu
250                 255                 260                 265 atg ggt gtg tca gag gag atg cag gca cgg gcc ctg gtg ctg cag ctg    870
Met Gly Val Ser Glu Glu Met Gln Ala Arg Ala Leu Val Leu Gln Leu
                270                 275                 280 tgg gcc aca cag ggg aat atg ggt ccc gct gcc ttc tgg ctc ctg ctc    918
Trp Ala Thr Gln Gly Asn Met Gly Pro Ala Ala Phe Trp Leu Leu Leu
            285                 290                 295 ttc ctt ctc aag aat cct gaa gcc ctg gct gct gtc cgc gga gag ctc    966
Phe Leu Leu Lys Asn Pro Glu Ala Leu Ala Ala Val Arg Gly Glu Leu
        300                 305                 310 gag agt atc ctt tgg caa gcg gag cag cct gtc tcg cag acg acc act   1014
Glu Ser Ile Leu Trp Gln Ala Glu Gln Pro Val Ser Gln Thr Thr Thr
315                 320                 325 ctc cca cag aag gtt cta gac agc aca cct gtg ctt gat agc gtg ctg   1062
Leu Pro Gln Lys Val Leu Asp Ser Thr Pro Val Leu Asp Ser Val Leu
330                 335                 340                 345 agt gag agc ctc agg ctt aca gct gcc ccc ttc atc acc cgc gag gtt   1110
Ser Glu Ser Leu Arg Leu Thr Ala Ala Pro Phe Ile Thr Arg Glu Val
                350                 355                 360 gtg gtg gac ctg gcc atg ccc atg gca gac ggg aga gaa ttc aac ctg   1158
Val Val Asp Leu Ala Met Pro Met Ala Asp Gly Arg Glu Phe Asn Leu
            365                 370                 375 cga cgt ggt gac cgc ctc ctc ctc ttc ccc ttc ctg agc ccc cag aga   1206
Arg Arg Gly Asp Arg Leu Leu Leu Phe Pro Phe Leu Ser Pro Gln Arg
        380                 385                 390 gac cca gaa atc tac aca gac cca gag gta ttt aaa tac aac cga ttc   1254
Asp Pro Glu Ile Tyr Thr Asp Pro Glu Val Phe Lys Tyr Asn Arg Phe
395                 400                 405 ctg aac cct gac gga tca gag aag aaa gac ttt tac aag gat ggg aaa   1302
Leu Asn Pro Asp Gly Ser Glu Lys Lys Asp Phe Tyr Lys Asp Gly Lys
410                 415                 420                 425 cgg ctg aag aat tac aac atg ccc tgg ggg gcg ggg cac aat cac tgc   1350
Arg Leu Lys Asn Tyr Asn Met Pro Trp Gly Ala Gly His Asn His Cys
```

```
                       430                435                440
ctg ggg agg agt tat gcg gtc aac agc atc aaa caa ttt gtg ttc ctt    1398
Leu Gly Arg Ser Tyr Ala Val Asn Ser Ile Lys Gln Phe Val Phe Leu
            445                 450                 455 gtg ctg gtg cac ttg gac ttg gag ctg atc aac gca gat gtg gag atc    1446
Val Leu Val His Leu Asp Leu Glu Leu Ile Asn Ala Asp Val Glu Ile
        460                 465                 470 cct gag ttt gac ctc agc agg tac ggc ttc ggt ctg atg cag ccg gaa    1494
Pro Glu Phe Asp Leu Ser Arg Tyr Gly Phe Gly Leu Met Gln Pro Glu
    475                 480                 485 cac gac gtg ccc gtc cgc tac cgc atc cgc cca tgacacaggg agcagatgga  1547
His Asp Val Pro Val Arg Tyr Arg Ile Arg Pro
490                 495                 500 tccacgtgct cgcctctgcc cagcctgccc cagcctgccc cagcctccca gctttctgtg  1607
tgcacagttg gcccgggtgc aggtgctagc attaccactt ccctgctttt ctcccagaag  1667
gctgggtcca ggggagggaa aagctaagag ggtgaacaaa gaaagacat tgaaagctct   1727 atggattatc cactgcaaag ttttctttcc aaaatcaggc tttgtctgct cccaattcac  1787
ctcgttactc tcacctcgtg atatccacaa atgctattca gataaggcag aactaggagt  1847
cttcactgct ctgcccccaa ctcccggagg tgtcaccttc ctagttctta tgagctagca  1907
tggcccgggc cttatccagt caaagcggat gctggccaca gaaaggccac tcaggatgtc  1967
ctttgtgtcc                                                        1977

<210> SEQ ID NO 15
<211> LENGTH: 500
<212> TYPE: PRT
<213> ORGANISM: Homo sapiens

<400> SEQUENCE: 15

Met Ala Trp Ala Ala Leu Leu Gly Leu Leu Ala Leu Leu Leu Leu
  1               5                  10                  15

Leu Leu Leu Ser Arg Arg Arg Thr Arg Arg Pro Gly Glu Pro Pro Leu
                 20                  25                  30

Asp Leu Gly Ser Ile Pro Trp Leu Gly Tyr Ala Leu Asp Phe Gly Lys
            35                  40                  45

Asp Ala Ala Ser Phe Leu Thr Arg Met Lys Glu Lys His Gly Asp Ile
        50                  55                  60

Phe Thr Ile Leu Val Gly Gly Arg Tyr Val Thr Val Leu Leu Asp Pro
    65                  70                  75                  80

His Ser Tyr Asp Ala Val Val Trp Glu Pro Arg Thr Arg Leu Asp Phe
                85                  90                  95

His Ala Tyr Ala Ile Phe Leu Met Glu Arg Ile Phe Asp Val Gln Leu
            100                 105                 110

Pro His Tyr Ser Pro Ser Asp Glu Lys Ala Arg Met Lys Leu Thr Leu
        115                 120                 125

Leu His Arg Glu Leu Gln Ala Leu Thr Glu Ala Met Tyr Thr Asn Leu
    130                 135                 140

His Ala Val Leu Leu Gly Asp Ala Thr Glu Ala Gly Ser Gly Trp His
145                 150                 155                 160

Glu Met Gly Leu Leu Asp Phe Ser Tyr Ser Phe Leu Leu Arg Ala Gly
                165                 170                 175

Tyr Leu Thr Leu Tyr Gly Ile Glu Ala Leu Pro Arg Thr His Glu Ser
            180                 185                 190

Gln Ala Gln Asp Arg Val His Ser Ala Asp Val Phe His Thr Phe Arg
```

```
                195                 200                 205
Gln Leu Asp Arg Leu Leu Pro Lys Leu Ala Arg Gly Ser Leu Ser Val
    210                 215                 220
Gly Asp Lys Asp His Met Cys Ser Val Lys Ser Arg Leu Trp Lys Leu
225                 230                 235                 240
Leu Ser Pro Ala Arg Leu Ala Arg Arg Ala His Arg Ser Lys Trp Leu
                245                 250                 255
Glu Ser Tyr Leu Leu His Leu Glu Glu Met Gly Val Ser Glu Glu Met
            260                 265                 270
Gln Ala Arg Ala Leu Val Leu Gln Leu Trp Ala Thr Gln Gly Asn Met
        275                 280                 285
Gly Pro Ala Ala Phe Trp Leu Leu Leu Phe Leu Leu Lys Asn Pro Glu
    290                 295                 300
Ala Leu Ala Ala Val Arg Gly Glu Leu Glu Ser Ile Leu Trp Gln Ala
305                 310                 315                 320
Glu Gln Pro Val Ser Gln Thr Thr Leu Pro Gln Lys Val Leu Asp
                325                 330                 335
Ser Thr Pro Val Leu Asp Ser Val Leu Ser Glu Ser Leu Arg Leu Thr
            340                 345                 350
Ala Ala Pro Phe Ile Thr Arg Glu Val Val Asp Leu Ala Met Pro
        355                 360                 365
Met Ala Asp Gly Arg Glu Phe Asn Leu Arg Arg Gly Asp Arg Leu Leu
    370                 375                 380
Leu Phe Pro Phe Leu Ser Pro Gln Arg Asp Pro Glu Ile Tyr Thr Asp
385                 390                 395                 400
Pro Glu Val Phe Lys Tyr Asn Arg Phe Leu Asn Pro Asp Gly Ser Glu
                405                 410                 415
Lys Lys Asp Phe Tyr Lys Asp Gly Lys Arg Leu Lys Asn Tyr Asn Met
            420                 425                 430
Pro Trp Gly Ala Gly His Asn Cys Leu Gly Arg Ser Tyr Ala Val
        435                 440                 445
Asn Ser Ile Lys Gln Phe Val Phe Leu Val Leu Val His Leu Asp Leu
450                 455                 460
Glu Leu Ile Asn Ala Asp Val Glu Ile Pro Glu Phe Asp Leu Ser Arg
465                 470                 475                 480
Tyr Gly Phe Gly Leu Met Gln Pro Glu His Asp Val Pro Val Arg Tyr
                485                 490                 495
Arg Ile Arg Pro
        500

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 16
gacaaggacc acatgtgcag tgtc                                          24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer
```

```
<400> SEQUENCE: 17
ctgtgtggcc cacagctgca gcac                                          24

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ile Glu Ala Leu Pro Arg Thr His Glu Ser Gln
 1               5                  10

<210> SEQ ID NO 19
<211> LENGTH: 12
<212> TYPE: PRT
<213> ORGANISM: Bos sp.

<400> SEQUENCE: 19

Gly Val Glu Ala Pro Pro His Thr Gln Glu Ser Gln
 1               5                  10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Cys Gly Ile Glu Ala Leu Pro Arg Thr His Glu Ser Gln
 1               5                  10
```

ANTIBODIES SPECIFIC TO HUMAN PROSTACYCLIN SYNTHASE

This application is a continuation-in-part application of U.S. Ser. No. 10/608,536 filed Jun. 30, 2003, in turn a continuation of U.S. Ser. No. 09/670,582 filed Sep. 27, 2000 (now abandoned), in turn a continuation of U.S. Ser. No. 09/037,758, filed Mar. 10, 1998 (now abandoned), in turn a divisional of U.S. Ser. No. 08/578,709 filed Dec. 28, 1995 (now U.S. Pat. No. 5,814,509).

BACKGROUND OF THE INVENTION

Technical Field

The present invention relates to a polypeptide having an amino acid sequence of human-originated prostacyclin synthase (hereinafter referred to as PGIS), a DNA encoding same, a vector containing said DNA, a host cell transformed with said vector and a method for preparing human-originated PGIS comprising culturing said host cell. The present invention also relates to an antibody having a reactivity with said PGIS or its fragment. Moreover, the present invention relates to a pharmaceutical composition comprising said DNA or a vector containing said DNA, a method for promoting the production of prostaglandin $I_2$ and a method for the treatment of the diseases induced by a low production of prostaglandin $I_2$.

PGIS is mainly contained in microsomal fractions of vascular endothelial cells, and is an enzyme that catalyzes synthesis of prostaglandin $I_2$ (hereinafter referred to as $PGI_2$), that is, conversion of prostaglandin $H_2$ (hereinafter referred to as $PGH_2$) to $PGI_2$.

$PGI_2$ synthesized by this enzyme has potent platelet aggregation-inhibitory action and vascular smooth muscle-relaxing action. On the other hand, platelets contain thromboxane $A_2$ (hereinafter referred to as $TXA_2$) having strong platelet aggregation action and vascular smooth muscle-contracting action, and the both substances act antagonistically in the vascular system to maintain homeostasis [British Journal of Pharmacology, vol. 76, p 3 (1982)].

Cardiovascular diseases such as myocardial infarction, thrombosis and arteriosclerosis, which are among the adult diseases, have recently been considered to be caused by the imbalance in the vascular production of $PGI_2$ and $TXA_2$, particularly, insufficient vascular function due to low production of $PGI_2$ (ibid.).

For the therapeutic treatment of the diseases presumably induced by the low production of $PGI_2$, $PGI_2$ may be supplemented as a pharmaceutical product from the outside of the body. However, $PGI_2$ is chemically extremely unstable to the extent that a practical use of $PGI_2$ itself as a pharmaceutical product may be unrealizable. In view of such situation, for example, stable $PGI_2$ analogs such as blood coagulation inhibitor or vasodilator are under development.

The homeostasis in human and other animals which is inherently based on the balance between $PGI_2$ and $TXA_2$ may possibly destroyed by the administration of stable $PGI_2$ analogs. That is, administration of stable $PGI_2$ analogs in large amounts is associated with a risk of lowering the responsiveness of cells to $PGI_2$, thus impairing its capability of responding to $PGI_2$ when such responsiveness is in urgent need [Prostaglandins, vol. 19, p 2 (1980)].

For correcting the imbalance between $PGI_2$ and $TXA_2$ and attempting the recovery of normal functions of the vascular system in an expectation of therapeutic effect over thrombosis and the like, chemically stable analogs may be used. Alongside therewith, moreover, elucidation of physico-chemical property and biological property of PGIS, clarification of the relations between PGIS production and $PGI_2$ production while using said PGIS or DNA encoding PGIS as a research sample, and development of said PGIS or DNA encoding PGIS as pharmaceutical products to regulate the production of $PGI_2$ are considered to be important and significant for the treatment of the above-said various diseases caused by the imbalance between $PGI_2$ and $TXA_2$.

Conventionally, there has been reported the tissue distribution of PGIS, namely, its presence in vascular endothelial cells, non-vascular smooth muscle cells and arterial smooth muscle of various organs [Advances in Prostaglandin, Thromboxane, and Leukotriene Research, vol. 11, pp. 87–92 (1983) and J. Biol. Chem., vol. 258, No. 9, pp. 5922–5926 (1983)]. Meanwhile, isolation and purification of PGIS from porcine and bovine have been tried [porcine: Cytochrome P450, Biochemistry, Biophysics and Environmental Implications, pp. 103–106 (1982); bovine: J. Biol. Chem., vol. 258, No. 9, pp. 3285–3293 (1983)] and N-terminal amino acid sequence and partial downstream amino acid sequence of bovine PGIS have been reported [Advances in Prostaglandin, Thromboxane, and Leukotriene Research, vol. 17, pp. 29–33 (1987) and Biochemical and Biophysical Research Communications, vol. 197, No. 3, pp. 1041–1048 (1993)].

However, isolation, purification and amino acid sequence of human PGIS have not been elucidated.

DISCLOSURE OF THE INVENTION

An object of the present invention is to clarify an amino acid sequence of PGIS derived from human and provide said human-originated PGIS and DNA encoding said PGIS.

Said PGIS and DNA encoding said PGIS are useful as reagents for (1) the analysis of the physicochemical and biological properties of PGIS at the molecular or genetic level; (2) the analysis of the mechanism controlling the production of PGIS and the mechanism controlling the production of $PGI_2$ by PGIS; and (3) the investigation of the cause of various cardiovascular diseases considered to be induced by the production imbalance between $PGI_2$ and $TXA_2$, and the molecular or genetic level analysis for the development of therapeutic agents for said diseases. In addition, PGIS and its mRNA are useful as diagnostics for the determination of expression level and distribution in the body tissues. Still further, they are expected to provide therapeutic agents for, for example, various cardiovascular disorders such as thrombosis, myocardial infarction, arteriosclerosis and angina pectoris, which enhance the production level of $PGI_2$ upon introduction of themselves, fragment thereof or modified compound thereof into the body in a lesion-specific manner.

Another object of the present invention is to provide a recombinant vector containing a DNA encoding human-originated PGIS, the expression system of PGIS which comprises a host cell transformed with said vector, and a method for preparing PGIS by genetic engineering using said expression system.

According to such method, human-originated PGIS can be prepared in great amounts with ease and with high efficiency.

The present invention also aims at providing a human-originated PGIS antibody useful for the purification of human-originated PGIS and immunohistochemical analysis of the cause of a disease.

The present inventor has conducted intensive studies with the aim of accomplishing the above-mentioned objects, and succeeded in cloning cDNA encoding PGIS from human aorta endothelial cells and identifying the primary structure of human-originated PGIS from the nucleotide sequence of said cDNA, which resulted in the completion of the present invention.

Accordingly, the present invention relates to a DNA comprising a DNA having a nucleotide sequence encoding an amino acid sequence of human-originated PGIS substantially depicted in SEQ ID NO: 15, preferably a DNA comprising a DNA having a 28th–1527th nucleotide sequence substantially shown in SEQ ID NO: 14, and more preferably a DNA having a 28th–1527th nucleotide sequence shown in SEQ ID NO: 14.

The present invention also relates to a recombinant vector comprising the above-mentioned DNA, a host cell transformed with said vector and a method for preparing human-originated PGIS comprising culturing said host cell in a medium and recovering human-originated PGIS from the obtained culture.

The present invention also relates to a polypeptide having an amino acid sequence of human-originated PGIS which is substantially shown in SEQ ID NO: 15, and antibodies having reactivities with said human-originated PGIS.

The present invention further relates to a pharmaceutical composition comprising said DNA or a recombinant vector comprising said DNA. Said pharmaceutical composition can be used as a medicament for promoting $PGI_2$ production or for treating the diseases induced by a low production of $PGI_2$.

The present invention moreover relates to a method for promoting the production of $PGI_2$, comprising introducing the above-mentioned DNA or a recombinant vector comprising said DNA into human or other animals. The present invention also relates to a method for treating the diseases induced by a low production of $PGI_2$, comprising introducing the above-mentioned DNA or a recombinant vector comprising said DNA into human or other animals.

DETAILED DESCRIPTION OF THE INVENTION

Figure 1:
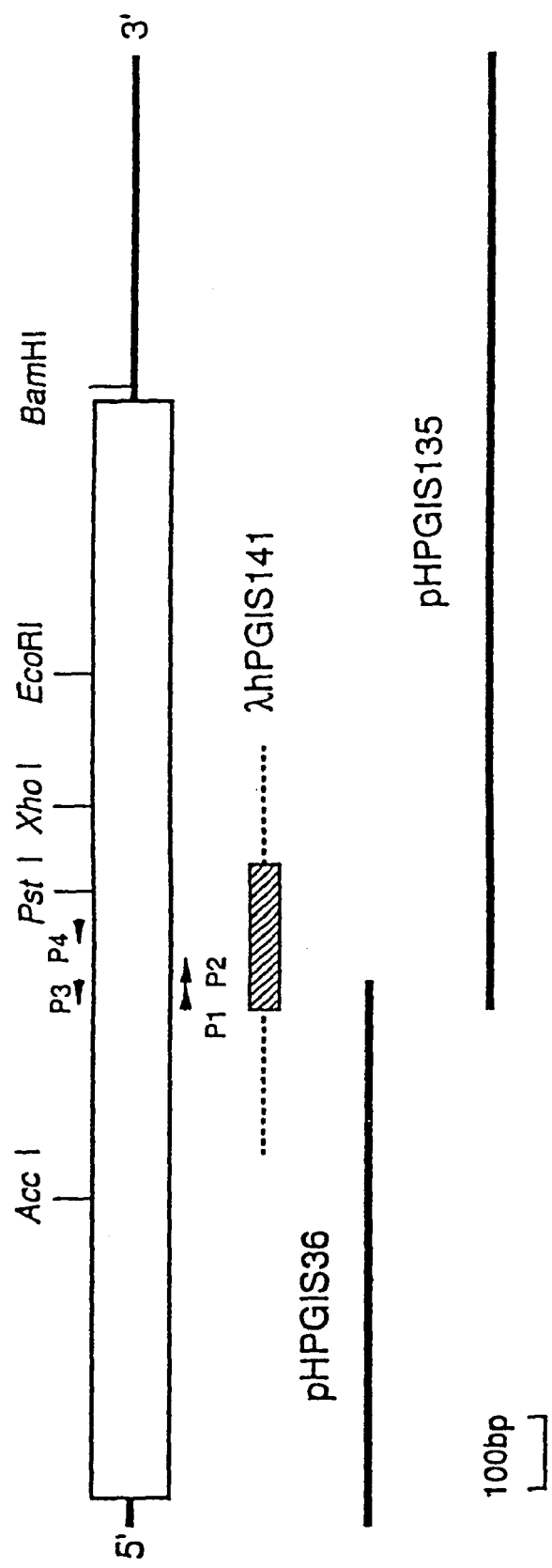
FIG. 1 shows a restriction enzyme map of human PGIS cDNA, and the PGIS DNA region comprised in λ hPGIS141, pHPGIS135 and pHPGIS36.

The present invention is explained in detail in the following.

The polypeptide of the present invention has a catalytic activity to convert $PGH_2$ to $PGI_2$ and has an amino acid sequence of human-originated PGIS substantially shown in Sequence Listing, SEQ ID NO: 15 to be mentioned later.

By "substantially" is meant that the polypeptide of the present invention is not limited to the polypeptide having the amino acid sequence shown in SEQ ID NO: 15, but may include deletion, substitution and addition with respect to some of the amino acids in the amino acid sequence shown in SEQ ID NO: 15, as long as the polypeptide has immunological and biological activity (human PGIS activity) similar to that of human-originated PGIS having said amino acid sequence.

While the site of deletion, substitution and addition of the amino acids is not particularly limited, at least 441st Cys residue and thereabout region in the amino acid sequence shown in Sequence No. 15 need to be reserved. This is because human-originated PGIS of the present invention is homologous to known cytochrome P450 in the amino acid sequence, since it has Cys residue in the C-terminal side of the amino acid sequence constituting the heme-binding site (fifth ligand) which is important for the expression of biological activity of cytochrome P450, and speculated to be a new protein belonging to the cytochrome P450 family [see Seibutsu Butsuri, vol. 32, No. 1, pp. 10–15 (1992)].

The polypeptide of the present invention preferably has an amino acid sequence of human-originated PGIS shown in SEQ ID NO: 15.

The PGIS activity possessed by the polypeptide of the present invention is a catalytic activity to convert $PGH_2$ to $PGI_2$. Said PGIS activity can be determined according to the method of Salmon, J. A. and Flower, R. J. et al [Methods Enzymol., 86, pp. 91–99 (1982)] wherein the conversion of $^{14}C$-labeled $PGH_2$ to $PGI_2$ is assayed by separating the metabolite of 6-keto-$PGF_1\alpha$. by thin layer chromatography and detecting the radioactivity of said 6-keto-$PGF_1\alpha$.

The present invention also relates to a DNA comprising a DNA having a nucleotide sequence encoding the amino acid sequence of human-originated PGIS substantially shown in SEQ ID NO: 15.

Said DNA may be any as long as it comprises a DNA having a nucleotide sequence encoding the aforementioned amino acid sequence of human-originated PGIS, and is exemplified by a DNA encoding the polypeptide having the amino acid sequence shown in SEQ ID NO: 15 or a polypeptide having the equivalent immunological and biological activity. More specifically, it is a DNA comprising the 28th–1527th nucleotide sequence in the nucleotide sequence shown in SEQ ID NO: 14.

In general terms, the genetic recombinant technique enables conversion of at least one nucleotide of a DNA sequence of a gene to a different nucleotide according to the degeneracy of the genetic code, without changing the amino acid sequence of a protein produced by the gene. Accordingly, the DNA of the present invention encompasses a DNA comprising a nucleotide sequence obtained by modification for substitution, based on the genetic code, of the 28th–1527th nucleotide sequence of Sequence Listing SEQ ID NO: 14.

The DNA of the present invention can be obtained by any method. For example, the present invention encompasses complementary DNA (cDNA) prepared from mRNA, DNA prepared from genomic DNA, DNA obtained by chemical synthesis, DNA obtained by amplification by PCR using RNA or DNA as a template, and DNA constructed by suitably combining these methods.

The DNA of the present invention can be obtained by a method comprising cloning cDNA from mRNA of human-originated PGIS by a conventional method, a method comprising splicing an isolated genomic DNA for PGIS, a method comprising chemical synthesis or other method.

(1) For example, a method for cloning cDNA from mRNA encoding human-originated PGIS comprises the following steps.

Cells producing human-originated PGIS, such as human aorta endothelial cells are cultured and mRNA encoding said PGIS is prepared from the culture thereof. mRNA is prepared by, for example, applying entire RNA prepared by a known method such as guanidine thiocyanate method [Chirgwin, J. M. et al., Biochem., 18, 5294 (1979)], heat phenol method and AGPC to affinity chromatography using oligo (dT)-cellulose or poly U-sepharose.

Using the obtained mRNA as a template, cDNA chain is synthesized by a known method using a reverse transcriptase [e.g., the method of Okayama, H. et al: Okayama, H. et al., Mol. Cell. Biol., 2, 161 (1982) and ibid. 3, 280 (1983), and the method of Gubler, U. and Hoffman, B. J.: Gubler, H. and Hoffman, B. J., Gene, 25, 263 (1983)], thereby converting the same to a double stranded cDNA. This cDNA is inserted into a plasmid vector or a phage vector, with which *Escherichia coli* is transformed, or transfected after in vitro packaging, to prepare cDNA library.

The plasmid vector used here is not subject to any particular limitation as long as it can be retained by replication in the host, and the phage vector is not limited either as long as it can proliferate in the host. Examples of the conventionally-used cloning vector include pUC119, λ gt10 and λ gt11. When immunological screening to be mentioned later is to be employed, the vector preferably contains a promoter capable of expressing the PGIS gene in the host.

The method for insertion of a cDNA into plasmid is exemplified by a method described in Maniatis, T. et al [Molecular Cloning, A Laboratory Manual, Cold Spring Harbor Laboratory, p. 239 (1982)]. The method for insertion of a cDNA into phage vector includes the method of Hyunh, T. V. et al [DNA Cloning, a practical approach, 1, 49 (1985)]. For simplification, a commercially available ligation kit (e.g., those manufactured by Takara Shuzo) can be used. The recombinant plasmid and phage vector thus obtained are introduced into a suitable host such as prokaryotic cells (e.g., *E. coli* HB101, DH5 and MC1061/P3).

The method for introducing a plasmid into a host includes calcium chloride method and calcium chloride/rubidium chloride method described in Maniatis, T. et al [Molecular Cloning, A Laboratory Manual, Cold Spring Harbor Laboratory, p. 239 (1982)] and electroporation method. The method for introducing a phage vector into a host is exemplified by a method comprising in vitro packaging of phage DNA and introducing same into proliferated host cells. In vitro packaging can be carried out easily by using a commercially available in vitro packaging kit (e.g., product of Stratagene and product of Amersham).

The cDNA encoding the PGIS of the present invention can be isolated from the cDNA library prepared by the above method, by a combination of general cDNA screening methods.

Such methods include, for example, a method wherein an oligonucleotide considered to be corresponding to the amino acid sequence of human PGIS is chemically synthesized separately and labeled with $^{32}$P to give a probe, and a clone having the desired cDNA is screened by a known colony hybridization [Crunstein, M. and Hogness, D. S., Proc. Natl. Acid. Sci. USA, 72, 3961 (1975)] or plaque hybridization [Molecular Cloning, A Laboratory Manual, Cold Spring Harbor Laboratory, p. 239 (1982)]; and a method wherein PCR primer is prepared and a specific region of PGIS is amplified by PCR method, which is followed by selecting a clone having a DNA fragment encoding said region. When a cDNA library prepared using a vector (e.g. λ gt11 phage vector) capable of expressing cDNA is used, the objective clone can be selected based on an antigen-antibody reaction using the PGIS antibody of the present invention to be mentioned later. When large amounts of clone are treated, screening based on PCR is preferable.

The nucleotide sequence of DNA thus obtained can be determined by Maxam-Gilbert method [Maxam, A. M. and Gilbert, W., Proc. Natl. Acad. Sci. USA., 74, 560 (1977)] or synthetic dideoxynucleotide chain termination method using phage M13 [Sanger, F. et al, Proc. Natl. Acad. Sci. USA., 74, 5463–5467 (1977)]. The PGIS gene can be obtained by cleaving all or part thereof from the clone obtained above by using a restriction enzyme and the like.

(2) A preparation method comprising isolating DNA encoding PGIS from genomic DNA of human aorta vascular cells includes, for example, the following method.

Human aorta vascular cells are lysed preferably using SDS or protenase K, and DNA is deproteinized by repetitive extraction with phenol. RNA is preferably digested with ribonuclease. The obtained DNA is partially digested with a suitable restriction enzyme and the obtained DNA fragment is amplified by a suitable phage or cosmid to form a library. Then, the clone having the desired sequence is detected by, for example, a method using a DNA probe with a radioactive label, and a whole or partial PGIS gene is cleaved from said clone by using a restriction enzyme and the like.

(3) The DNA of the present invention can be prepared by chemical synthesis by a conventional method based on the nucleotide sequence depicted in Sequence Listing SEQ ID NO: 14.

The present invention further relates to a recombinant vector comprising DNA encoding the above-mentioned PGIS. The recombinant vector of the present invention is not particularly limited as long as it can be retained by replication or self-proliferation in various prokaryotic and/or eukaryotic host cells, and includes plasmid vector and phage vector.

The recombinant vector can be easily prepared by ligating the DNA encoding human-originated PGIS of the present invention with a commercially available recombinant vector (plasmid DNA and bacteriophage DNA) by a conventional method. Usable recombinant vector includes, for example, *Escherichia coli*-originated plasmids pBR322, pBR325, pUC12 and pUC13; yeast-originated plasmids pSH19 and pSH15; and *Bacillus subtilis*-originated plasmids pUB110, pTP5 and pC194. Examples of phage include bacteriophage such as λ phage, and animal or insect viruses such as retrovirus, vaccinia virus, nuclear polyhedrosis virus and adenovirus [e.g. pVL1392, pBK283, *Autographa californica* nuclear polyhedrosis virus (AcNPV) and *Bombyx mori* nuclear polyhedrosis virus (BmNPV)].

When production of PGIS by the expression of the PGIS gene is aimed, an expression vector is useful. The expression vector is not particularly limited as long as it expresses the PGIS gene in various prokaryotic and/or eukaryotic host cells and is capable of producing proteins. Preferred are that derived from insect virus which infects insect cells and produces PGIS in said cells, and that derived from animal virus which infects animal cells and produces PGIS in said cells.

When bacteria, particularly *Escherichia coli*, is used as the host cell, the expression vector generally consists of at least promoter-operator region, initiation codon, DNA encoding the PGIS of the present invention, termination codon, terminator region and replicon.

When yeast, animal cell or insect cell is used as the host cell, the expression vector preferably consists of at least promoter, initiation codon, DNA encoding the polypeptide of the present invention and termination codon. It may contain DNA encoding signal peptide, enhancer sequence, non-translation region on the 5' or 3' side of the polypeptide of the present invention, splicing junction, polyadenylation site, selection marker region, replicon and the like.

The promoter-operator region for expressing the polypeptide of the present invention in bacteria contains promoter, operator and Shine-Dalgarno (SD) sequence such as AAGG. When the host is *Escherichia coli*, the region preferably contains, for example, Trp promoter, lac promoter, recA promoter, λ PL promoter and lpp promoter. The promoter for expressing PGIS in yeast includes, for example, PH05 promoter, PGK promoter, GAP promoter and ADH promoter, and when the host is bacteria belonging to the genus *Bacillus*, SL01 promoter, SP02 promoter and penP promoter can be used. When the host is eukaryotic cells such as animal cells, examples of the promoter include, but not limited to, SV40-derived promoter, retrovirus promoter, heat shock promoter, polyhedron promoter that a nuclear polyhedrosis virus has, cytomegalovirus promoter, adenovirus promoter and β-actin promoter. The use of an enhancer is also effective for the expression.

Preferable initiation codon includes, for example, methionine codon (ATG).

The termination codon is exemplified by conventional termination codons such as TAG and TGA.

As the terminator region, conventional intact or synthetic terminator can be used.

By replicon is meant a DNA capable of reproducing the entire DNA sequence in the host cell, and exemplified by naturally occurring plasmid, artificially modified plasmid (DNA fragment prepared from naturally occurring plasmid) and synthetic plasmid. Examples of preferable plasmid include plasmid pBR322 and artificial modification thereof (DNA fragment obtained by treating pBR322 with a suitable restriction enzyme) in the case of *E. coli*; yeast 2μ plasmid and yeast chromosomal DNA in the case of yeast; and plasmid pRSVneo ATCC 37198, plasmid pSV2dhfr ATCC 37145, plasmid pdBPV-MMTneo ATCC 37224 and plasmid pSV2neo ATCC 37149 in the case of mammalian cell.

Enhancer sequence, polyadenylation site and splicing junction site can be those conventionally used by artisan, such as respective ones derived from SV40.

As the selection marker, conventional ones can be used according to a conventional method. Examples thereof include a gene resistant to antibiotic such as tetracycline, ampicillin and kanamycin.

The expression vector of the present invention can be prepared by ligating at least the above-mentioned promoter, initiation codon, DNA encoding PGIS of the present invention, termination codon and terminator region sequentially and cyclically into a suitable replicatable unit. For this end, suitable DNA fragments such as linker and other restriction sites can be used by a conventional method such as digestion with restriction enzyme and ligation using T4DNA ligase on demand.

The transformant of the present invention can be prepared by introducing the above-mentioned expression vector into a host cell.

Examples of the host cell include microorganisms such as bacteria (e.g. bacteria belonging to the genera *Escherichia* and *Bacillus*), yeast such as those belonging to the genus *Saccharomyces*, animal cells and insect cells. Specifically exemplified are *Escherichia coli* K12DH1, M103, JA221, HB101, C600, XL-1 Blue and JM109 as the bacteria belonging to the genus *Escherichia*; and *Bacillus subtilis* 207-21 as the bacteria belonging to the genus *Bacillus*. Examples of the yeast include *Saccharomyces cerevisiae* AH22, AH22R-, NA87-11A and DKD-5D. Examples of animal cell include simian cell COS-7, Vero, Chinese hamster cell CHO, mouse L cell, human FL cell and human 293 cell. Examples of insect cell include BmN4 and Sf9. Preferred are insect cells and animal cells.

The preferred host cell for cloning the DNA sequence and constructing the vector is generally a prokaryotic cell. The expression vector constructed is used to transform a suitable host cell. The host cell may be a prokaryotic cell or an eukaryotic cell as well. Preferred are insect cells (e.g., BmN4 and Sf) and animal cells.

The expression vector is introduced (i.e., transformation which is used in a concept inclusive of transfection in the present invention) into host cells by a conventionally known method.

For example, in the case of bacteria (e.g. *Escherichia coli* and *Bacillus subtilis*), the method of Cohen et al [Proc. Natl. Acad. Sci. USA., 69, 2110 (1972)] protoplast method [Mol. Gen. Genet., 168, 111 (1979)] or competent method [J. Mol. Biol., 56, 209 (1971)] may be used; in the case of *Saccharomyces cerevisiae*, the method of Hinnen et al [Proc. Natl. Acad. Sci. USA., 75, 1927 (1978)] or lithium method [J. Bacteriol., 153, 163 (1983)] may be used; in the case of animal cells, the method of Graham [Virology., 52, 456 (1973)], lipofectin method or HVJ-liposome method [Hypertension, 21, 894–899 (1993)] may be used; and in the case of insect cells, the method of Summers et al [Mol. Cell. Biol., 3, 2156–2165 (1983)] may be used for transformation.

The human-originated PGIS of the present invention can be prepared by culturing, in a nutrient medium, a transformant (which term is used in a concept inclusive of transfectant in the present invention) comprising the expression vector prepared as in the above.

The nutrient medium preferably contains carbon source, inorganic nitrogen source or organic nitrogen source necessary for the growth of host cell (transformant). Examples of carbon source include glucose, dextran, soluble starch and sucrose; examples of inorganic nitrogen source or organic nitrogen source include ammonium salts, nitric acid salts, amino acid, corn steep liquor, peptone, casein, meat extract, soybean meal and potato liquid extract. When desired, other nutrients such as inorganic salt (e.g. calcium chloride, sodium dihydrogenphosphate and magnesium chloride), vitamins, and antibiotics such as ampicillin and kanamycin may be added to the medium.

Culture is carried out according to the method known in the pertinent field. Culture conditions such as temperature, pH of the medium and culture time are appropriately determined so that the maximum potency of PGIS can be obtained.

Specific media and culture conditions to be employed according to the host cell are exemplified in the following, which are not limitative.

When the host is bacteria, Actinomyces, yeast or filamentous fungus, for example, liquid media containing the above-mentioned nutrient sources are appropriate. Preferred is a medium having a pH of 5–8.

When the host is *Escherichia coli*, preferable medium is M9 medium [Miller, J., Exp. Mol. Genet., p. 431, Cold Spring Harbor Laboratory, New York (1972)]. In this case, culture is performed with aeration and agitation as necessary, at 14° C.–43° C. for about 3 to 24 hours.

When the host is bacteria belonging to the genus *Bacillus*, culture is performed with aeration and agitation as necessary, at 30°–40° C. for about 16 to 96 hours.

When the host is yeast, the medium is exemplified by Burkholder minimum medium [Bostian, K. L. et al, Proc. Natl. Acad. Sci. USA, 77, 4505 (1980)] which preferably has a pH of 5–8. Culture is generally performed at about 20–35° C. for about 14 to 144 hours with aeration and agitation where necessary.

When the host is animal cell, the medium is exemplified by MEM medium containing fetal calf serum at about 5–20% [Science, 122, 501 (1952)], DMEM medium [Virology, 8, 396 (1959)], RPMI1640 medium [J. Am. Med. Assoc., 199, 519 (1967)] and 199 medium [Proc. Soc. Exp. Biol. Med., 73, 1 (1950)]. The pH of the medium is preferably about 6–8, and culture is generally performed at about 30° C.–40° C. for about 15–60 hours with aeration and agitation where necessary.

When the host is insect cell, the medium is exemplified by Grace's medium containing fetal calf serum [Proc. Natl. Acad. Sci. USA, 82, 8404 (1985)] which preferably has a pH of about 5–8. Culture is generally performed at about 20° C.–40° C. for about 15 to 100 hours with aeration and agitation where necessary.

The human-originated PGIS of the present invention can be recovered as in the following from the culture obtained above.

That is, when the human-originated PGIS is present in the liquid portion of the culture, the culture thus obtained is subjected to filtration or centrifugation to separate culture filtrate (supernatant), and PGIS is purified and separated from said culture filtrate by a conventional method employed for purifying and isolating natural or synthetic proteins.

The method for purification and isolation includes, for example, a method utilizing the solubility, such as salting out and solvent precipitation, a method utilizing the difference in molecular weights such as dialysis, ultrafiltration, gel filtration and sodium dodecyl sulfate-polyacrylamide gel electrophoresis, a method utilizing charge such as ion exchange chromatography and hydroxyapatite chromatography, a method utilizing specific affinity such as affinity chromatography, a method utilizing the difference in hydrophobicity such as reversed phase high performance liquid chromatography and a method utilizing difference in isoelectric point such as isoelectric focusing.

When the human-originated PGIS is present in the periplasm or cytoplasm of the cultured transformant, the culture is subjected to a conventional method such as filtration and centrifugation to collect the cells; the cells are suspended in a suitable buffer and subjected to lysis of cell wall and/or cell membrane by ultrasonication, using lysozyme or by freeze-thawing; and the membrane fraction containing PGIS is obtained by centrifugation or filtration. Said membrane fraction is solubilized with surfactant such as Triton to give a crude solution. The crude solution is treated by a conventional method as exemplified supra to isolate and purify PGIS of the present invention.

The present invention also relates to an antibody having a reactivity with the above-said human-originated PGIS. The antibody of the present invention encompasses both the polyclonal antibody and monoclonal antibody having the above-mentioned properties. The antibody of the present invention can be obtained by a conventional method.

For example, the monoclonal antibody of the present invention can be prepared from hybridoma produced by so-called cell fusion. That is, fused hybridoma is formed from the antibody-producing cell and bone marrow cell; said hybridoma is cloned; and a clone is selected which produces an antibody having a specific affinity for an antigen, i.e. a polypeptide having part or whole of the human-originated PGIS amino acid sequence. The procedure therefor may be known methods except the use of the human-originated PGIS of the present invention as an immunizing antigen.

The immunogen can be used for immunizing animals after admixing with, for example, complete Freund adjuvant. Examples of the animal include mouse, rat and rabbit. The animals are immunized by subcutaneous, intramuscular or intraperitoneal injection of about 5–200 μg/injection. The immunization includes 1–4 times of immunization at about every 1–2 weeks from the initial immunization and final immunization at about 1–4 weeks thereafter. When about 3–5 days have passed since final immunization, antibody-producing cells are separated from the immunized animal. The antibody-producing cells are exemplified by spleen cells and lymph node cells.

The bone marrow cells are, for example, those derived from mouse, rat and human. Examples thereof include mouse myeloma P3.X63.Ag8, P3.X63.Ag8-U1, P3.NS1-Ag4, SP2/0-Ag14 and X63-Ag8 . 653. It is preferable that the antibody-producing cells and bone marrow cells be derived from the same species of animals.

Cell fusion is performed by the method described in, for example, Nature, vol. 266, p. 550 (1977) or an analogous method. Specifically, it is performed using 30–50% polyethylene glycol having an average molecular weight of 1,000–4,000 at 30° C.–40° C. for about 1–3 minutes.

The cells obtained by cell fusion are subjected to screening for a clone which produces the desired monoclonal antibody. That is, the cells are cultured in, for example, a microplate and the antibody titer of the culture supernatant in the well in which cell growth was acknowledged is determined by, for example, enzyme antibody method to obtain the well in which suitable antibody has been produced. Cloning by, for example, limiting dilution from such well gives clones. The monoclonal antibody of the present invention can be obtained by culturing said hybridoma cell clone by conventional culture method, high density culture method or spinner-flask culture method and purification thereof by affinity chromatography using protein A-bound carrier or anti-mouse immunoglobulin-bound carrier.

Alternatively, the cultured hybridoma cells are intraperitoneally injected to the mouse of the same species which has been previously treated with pristance, and ascites obtained is subjected to salting out with ammonium sulfate and DEAE ion exchange chromatography to give purified IgG fraction containing the same.

The DNA encoding the human-originated PGIS of the present invention can be used for gene therapy.

The DNA encoding the human-originated PGIS of the present invention or a recombinant vector comprising said DNA is introduced into human or other animals, whereby PGIS is produced in the human or other animals to promote production of $PGI_2$. The promoted $PGI_2$ production in turn enables treatment (therapeutic treatment or improvement of symptoms) of the diseases induced by a low production of $PGI_2$. Examples of the diseases induced by the low production of $PGI_2$ include cardiovascular diseases such as thrombosis, myocardial infarction, arteriosclerosis and angina pectoris. The recombinant vector may be introduced into human or other animals in the form of cells transformed with said recombinant vector.

The gene therapy utilizing the gene (inclusive of DNA and recombinant vector) of the present invention permits setting an appropriate environment in which the gene of the present invention introduced into a human or other animal can fully show its function. The treatment can be given by a conventional method as long as it intends expression of desired effects of the gene of the present invention. Such method is exemplified by virological means utilizing retrovirus vector or adenovirus vector, physical means for introducing gene by particle gun method or by using naked DNA, and chemical means such as lipid method [Molecular Medicine, vol. 30, No. 12, p. 1526 (1993); Jikken Igaku, vol. 12, No. 3, p. 15, 28 and 40 (1994); Proc. Natl. Acad. Sci. USA, 92, 1137 (1995)]. A method using an adenovirus vector which can be used for the gene therapy of cystic fibrosis and which is known to permit efficient introduction of gene into differentiated cells and tissues and expression therein, and a method using a fusogenic liposome which allows introduction of optional gene into tissue cells in vivo are preferable for the gene treatment of the present invention.

The dose of the DNA or recombinant vector of the present invention is subject to appropriate change according to sex, age and body weight of patients, the kind of disease and symptoms thereof, and administration route. For example, 100 µg–10 mg of DNA is generally administered.

The DNA and recombinant vector of the present invention are administered by intravenous injection, transmucosal administration, oral administration using enteric-coated agents, or topical administration, with preference given to topical administration using catheter and the like.

The DNA encoding human-originated PGIS and recombinant vector comprising said DNA of the present invention are admixed with conventional, pharmaceutically acceptable carrier, excipient, diluent, extender, disintegrator, stabilizer, preservative, buffer, emulsifier, flavor, coloring, sweetener, thickener, elixir, solubilizer and other additives such as water, salt solution, phosphate buffer, vegetable oil, ethanol, polyethylene glycol, glycerol, gelatin, lactose, glucose, mannitol, starch, sucrose, magnesium stearate, hydroxypropylcellulose, talc, lanolin and petrolatum, and can be used in the form of injection, tablet, powder, capsule, enteric-coated agent, ointment, suspension, emulsion, spray, inhalant, collunarium and the like.

A pharmaceutical composition comprising the DNA or recombinant vector comprising said DNA of the present invention can be administered to mammals such as human, mouse, rat, rabbit, pig, cow, sheep, dog and cat.

EFFECTS OF THE INVENTION

The present invention gives the first clarification of the amino acid sequence of human-originated PGIS and nucleotide sequence of DNA encoding the enzyme having said sequence. Based on the elucidation of such amino acid sequence and nucleotide sequence, the present invention provides a method for preparing PGIS by genetic engineering and an expression system related thereto.

The PGIS and DNA encoding same of the present invention are useful as reagents for (1) the analysis of physicochemical property and biological property of PGIS at the molecular or genetic level, (2) the analysis of the mechanism of regulating PGIS production and the mechanism of regulating $PGI_2$ production by PGIS, and (3) the investigation of the cause of various cardiovascular diseases considered to be induced by the production imbalance between $PGI_2$ and $TXA_2$, and analysis at the molecular or genetic level for the development of therapeutic agent for said diseases.

In addition, they are useful as diagnostics for determining the in vivo tissue expression level and distribution of PGIS or mRNA thereof.

Moreover, they can be used as therapeutic agents for various cardiovascular diseases such as thrombosis, myocardial infarction, arteriosclerosis and angina pectoris, which increase the production level of $PGI_2$ based on lesion-specific introduction, into human and other animals, of PGIS, DNA encoding PGIS, fragment thereof or modified product thereof.

The expression system of PGIS comprising a recombinant vector containing DNA encoding the human-originated PGIS of the present invention, and a host cell transformed with said vector is useful for the production by genetic engineering, which enables easy and efficient mass production of human-originated PGIS.

In addition, the human-originated PGIS antibody of the present invention serves well for the purification of human-originated PGIS and the immunohistochemical analysis of the cause of a disease (specific staining of various tissues such as uterus, heart, skeletal muscle, lung and prostate).

The plasmid, enzyme such as restriction enzyme, T4DNA ligase and other substances to be used in Examples of the present invention are commercially available and can be used according to a conventional method. The procedures for cloning of cDNA, determination of nucleotide sequence, transfection of host cell, culture of transfectant, harvesting and purification of PGIS from obtained culture, and obtainment of antibody are well known to those skilled in the art, or can be known from literatures.

The pHPGIS36 (PBJT-BA-4, deposit number FERM BP-4653) and pHPGIS135 (PBJT-BA 5, deposit number FERM BP-4654) used in the present invention are at international deposit at National Institute of Bioscience and Human-Technology Agency of Industrial Science and Technology.

EXAMPLES AND REFERENCE EXAMPLES

The present invention is described detailedly in the following by way of Examples and Reference Examples, to which the present invention is not limited.

Example 1

Determination of cDNA Nucleotide Sequence (1) Preparation of λ hPGIS141

Human genomic library (Genomic lung fibroblast cell line, W I 38, manufactured by Clone-Tech) was seeded at about $2 \times 10^5$ PFU, and screened by plaque hybridization using, as a probe, a bovine cDNA prepared in advance by the inventor (see Tanabe, T., Hara, S., Miyata, A., Brugger, R., and Ullrich, V. (1993) in Abstract book of 3rd international conference on eicosanoid and other bioactive lipids in cancer, inflammation and radiation Injury, p. 137).

As a result, four positive signals were obtained, one of which was isolated to a single plaque. Liquid culture thereof resulted in mass preparation of phage DNA. After purification, it was digested with various restriction enzymes, followed by mapping. A fragment comprising exon was identified by Southern hybridization, which was followed by structural analysis by DNA sequencing to confirm that the finally-isolated clone (λ hPGIS141) coded for human PGIS.

The λ hPGIS141 thus obtained was structurally analyzed by restriction enzyme site mapping and nucleotide sequence determination, and it was found that λ hPGIS141 contained the region corresponding to a 673rd–855th nucleotide sequence of bovine PGIS cDNA (SEQ ID NO: 8) corresponding to amino acid SEQ ID NO: 9.

Based on the nucleotide sequence of λ hPGIS141 cDNA fragment thus obtained, primers [SEQ ID NO: 1: P1 primer (674–689), SEQ ID NO: 2: P2 primer (699–718), SEQ ID NO: 3: P3 primer (696–713), SEQ ID NO: 4: P4 primer (805–822)] having the sequences depicted in Sequence List SEQ ID NOS: 1–4 were synthesized.

(2) Amplification of cDNA by PCR Method

The 3'-downstream region and 5'-upstream region of cDNA were amplified by PCR method [Biochem. Biophys. Res. Commun. 178, 1479–1484 (1991)] using said primers and poly(A)$^+$ RNA (mRNA) from 1 μg of human aorta vascular endothelial cells (hereinafter referred to as HAEC, manufactured by Kurabo) as a template.

For amplification of cDNA corresponding to the 3'-downstream region, cDNA was primed with a $dT_{17}$ adapter (5'-GACTCGAGTCGACATCGA-$(T)_{17}$-3', SEQ ID NO: 5), and elongated to give a first cDNA chain which was amplified with P1 primer (674–689) and the adapter primer (SEQ ID NO: 6), and then with P2 primer (699–718) and the adapter primer (SEQ ID NO: 6). The 5'-upstream region of the cDNA was amplified using a 5' RACE system (GIBCO BRL). According to the protocol, homomeric dC tail was added to the first cDNA chain and a second cDNA chain was formed using an adapter primer (5'-$(CUA)_4$ GGC-CACGCGTCGACTAGTACGGGIIGGGIIGGGIIG-3') (SEQ ID NO: 7). The first step amplification was performed using P4 primer and the adapter primer (SEQ ID NO: 7). The second step amplification was performed using P3 primer and the adapter primer (SEQ ID NO: 7). The PCR method was repeated 35 cycles according to the following cycloprofile.

| | |
|---|---|
| Denaturation | 94° C., 1 minute |
| Annealing | 54° C., 1 minute |
| Elongation | 72° C., 3 minutes |

The respective PCR products (3'-downstream region amplification product and 5'-downstream region amplification product) were partially taken out and purified by electrophoresis using 1% agarose gel. Southern hybridization was applied using bovine cDNA (pBPGISI) as a probe, and DNA was extracted from the band which cross-hybridized to said probe. The obtained DNA was cloned into pBluescriptII SK(-).

That is, cloning and screening were performed by the following steps:

(1) cleaving out the band which showed a signal from a gel, after electrophoresis
(2) agarase digestion at 40° C. for one hour (agarase 1 unit/100 μl gel)
(3) extraction of DNA with phenol and subsequent ethanol precipitation
(4) dissolving said DNA ethanol precipitate in sterile water and treating with polynucleotide kinase at 37° C. for one hour
(5) end repairing with Klenow fragment (16° C., 1 hr)
(6) ligation using Takara ligation kit
(7) transformation by a conventional method
(8) sewing in a plate
(9) forming a replica by a conventional method and
(10) colony hybridization of nitrocellulose filter of the replica by a conventional method, using bovine PGIS cDNA as a probe The hybridization was performed at 60° C. in 6×SSC [1×SSC containing 0.15 M NaCl, 15 mM sodium citrate (pH 7.0)], 5× Denhardt's solution, 250 μg/ml salmon sperm DNA, 0.1% SDS and cDNA fragment ($10^6$ cpm/ml) labeled by random priming method. The filter obtained was washed twice with 3×SSC and 0.1% SDS at room temperature for 5 minutes and twice with 0.1×SSC and 0.1% SDS at 50° C. for 15 minutes. The filter was air-dried, and exposed to Fuji X ray film using a intensifying screen at -80° C. for 12–16 hr.

The obtained DNA insert was subcloned into pBluescriptII SK(-). By these steps, a clone (pHPGIS135) containing 3'-downstream region DNA of human-originated PGIS and a clone (pHPGIS36) containing 5'-upstream region DNA of human-originated PGIS were obtained. Then, the nucleotide sequence of the DNA insert of respective clones was determined by the Sanger method [Sanger, F., Nickle, S., and Coulson, A. R. (1977) Proc. Natl. Acad. Sci. USA 74, 5463–5467] using Taq dye primer cycle sequence kit (manufactured by Applied Biosystems) and Model 373A DNA sequencer (manufactured by Applied Biosystems). As a result, it was found that pHPGIS36 clone had, as a DNA insert sequence, a 740 bp nucleotide sequence (SEQ ID NO: 10) of cDNA of human PGIS, having an adapter sequence on the 5' side, based on which partial amino acid sequence of PGIS comprising 237 amino acid residues wherein ATG is the translation initiation sequence (Met) was identified.

Figure 2:
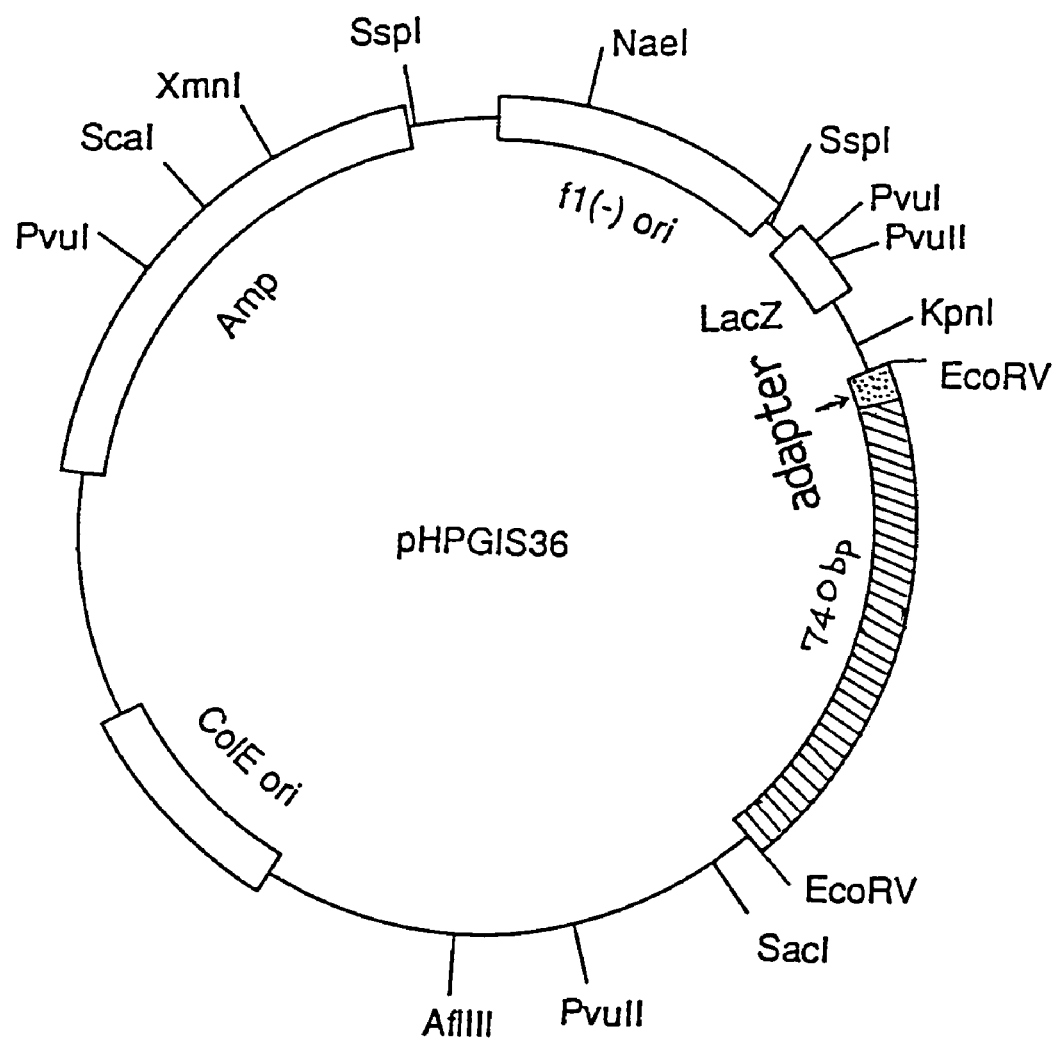
FIG. 2 shows a restriction enzyme map of plasmid pHPGIS36.
Figure 3:
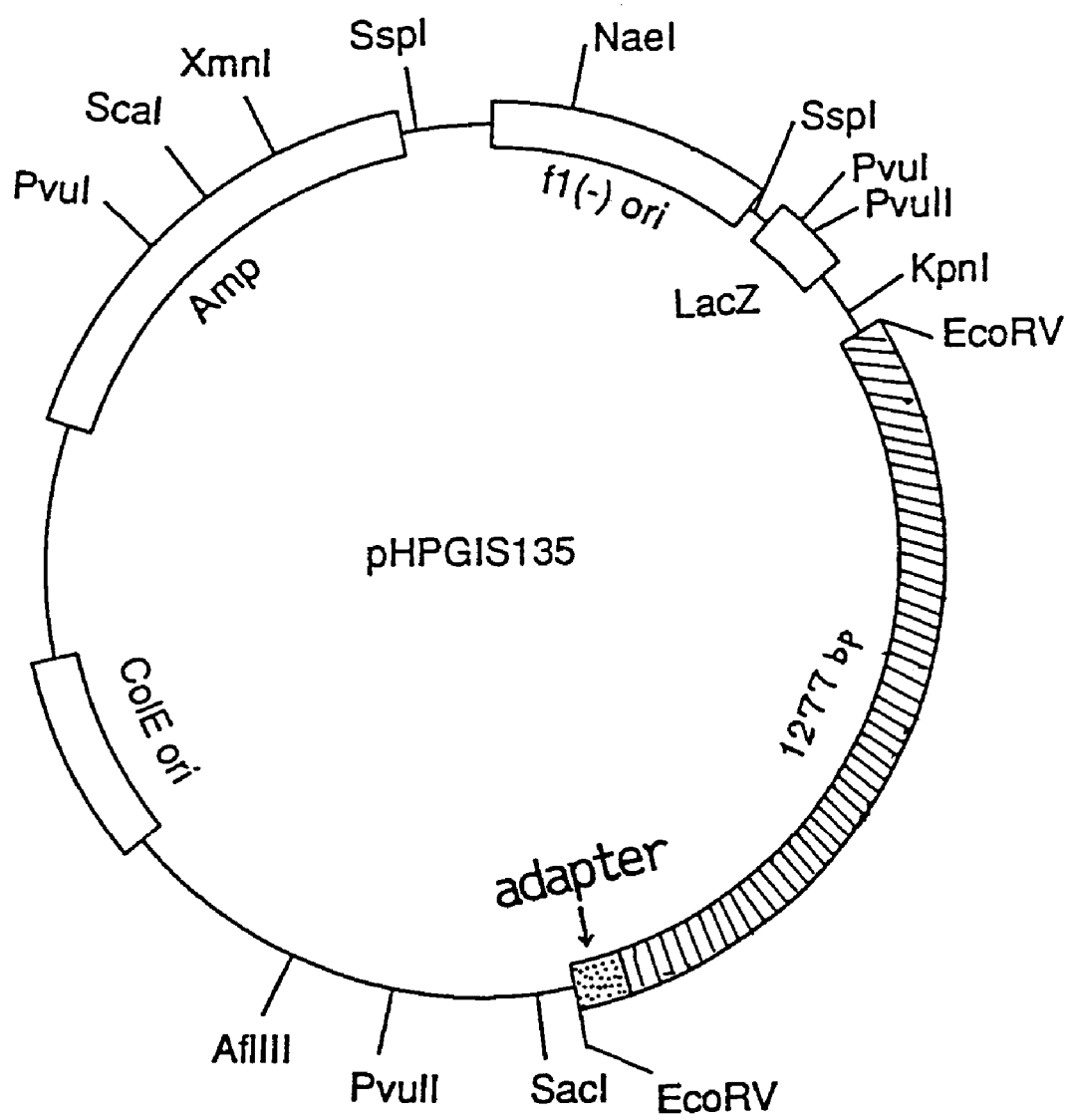
FIG. 3 shows a restriction enzyme map of plasmid pHPGIS135.

It was also found that pHPGIS135 clone comprised, as a DNA insert sequence, a 1277 bp nucleotide sequence (SEQ ID NO: 12) of cDNA of human PGIS, having an adapter sequence on the 3' side, based on which partial amino acid sequence of PGIS on the carboxyl side region starting from 226th aspartic acid was identified. The nucleotide sequence of human PGIS cDNA contained in pHPGIS36 clone and the amino acid sequence deduced therefrom are depicted in SEQ ID NO: 11 in the Sequence Listing to be mentioned later, and the nucleotide sequence of human PGIS cDNA contained in pHPGIS 135 clone and the amino acid sequence deduced therefrom are depicted in SEQ ID NO: 13 therein. FIG. 1 shows a restriction enzyme map of human PGIS cDNA and the region of human PGIS cDNA, which corresponds to the DNA contained in λ hPGIS141, pBPGIS36 and pHPGIS135. FIG. 2 shows a restriction enzyme map of pHPGIS36 and FIG. 3 shows a restriction enzyme map of pHPGIS135.

Human PGIS cDNA obtained by the above-mentioned cloning had a consensus sequence of the initiation codon of eukaryotic shown by Kozak et al [Nucleic Acids Res. 12, 857–872 (1984)] at around the translation initiation codon, and TGA codon corresponding to the termination codon at 500 codons therefrom. Based on these facts, it was found that the cDNA of the cloned human PGIS comprised 1977 bp comprising 1500 bp encoding 500 amino acid residues, as shown in SEQ ID NO: 15, and the molecular weight of the protein coded thereby was speculated to be about 57,000.

Comparison of the amino acid sequence encoded by said DNA with the amino acid sequence of bovine-originated PGIS separately cloned by the present inventor revealed an about 88% homology. The study of bovine PGIS by the present inventor found that the bovine PGIS had a 31% homology with cholesterol 7α-hydroxylase belonging to the cytochrome P450 7 family (CYP7), and the region around the 441st Cys residue, which is heme-binding site (fifth ligand) of cytochrome P450, was reserved. The human PGIS similarly reserved the amino acid sequence corresponding to said region, and this region is considered to play an important role in the PGIS activity.

Although the bovine PGIS had a 31% homology with cholesterol 7α-hydroxylase, it had only a 16% homology with human thromboxane synthase belonging to the cytochrome P450 family and a not more than 40% homology with any of the known cytochrome P450 proteins. It is postulated, therefore, that it is a new family in the cytochrome P450 super family, and human PGIS also belongs to this new family.

A search for such structural correlation in activity is indispensable for the study and development of pharmaceutical products. Such search is accomplished only after the primary structure of human PGIS has been clarified. Accordingly, the present invention which discloses the primary structure of human PGIS for the first time is extremely important and significant for the research, and from industrial aspect as well.

Example 2

Expression of Human PGIS (1) Construction of Expression Vector for Human PGIS

A cDNA insert region is cleaved out respectively from the obtained pHPGIS36 clone and pHPGIS135 clone using a suitable restriction enzyme, and purified. The both fragments obtained were thermally denatured (95° C. for 10 minutes), followed by annealing. cDNA is replicated using a DNA polymerase to the both directions toward 5' and 3' from the overlapped region as the synthesis initiation region. Using the obtained whole length cDNA as a template, a primer is synthesized from each region of initiation codon or termination codon and PCR is performed. On this occasion, a suitable restriction enzyme site is constructed as an anchor site at 3' of the primer.

The PCR product thus obtained is purified, the nucleotide sequence of which is confirmed, and the product is digested with BamHI and SmaI (BglII) to give a BamHI-SmaI (BglII) fragment. Said BamHI-SmaI (BglII) fragment is introduced into the BamHI-SmaI site of pVL1393 expression vector previously treated with BamHI-SmaI. The recombinant plasmid thus formed (PGIS7) is characterized by restriction enzyme mapping and DNA sequence analysis.

(2) Baculovirus Expression System

Sf9 cells (manufactured by In Vitrogen) are mono-layer cultured in a Grace's insect medium containing 10% fetal calf serum, 0.33% yeastolate and 0.33% lactoalbumin hydrolysate at 27° C. For the production of a recombinant virus, Sf9 cell ($1.5 \times 10^6$ cells) recombinant plasmid (PGIS7, 50 μg) and wild type baculovirus DNA (AcNPV; 1 μg) are mixed and transfected by calcium phosphate precipitation method. The recombinant baculovirus is isolated and amplified by a combination of plaque assay and slot hybridization using a $^{32}$P-labeled cDNA fragment of PGIS as a probe.

Said Sf9 cells are infected with wild type baculovirus or recombinant baculovirus. At 3 days after the infection, cells are collected ($2 \times 10^8$ cells) and incubated for 5 hours in a serum-containing medium with or without 10 μM hemin.

The obtained cells are washed with phosphate-buffered saline and preserved at −80° C. The microsomal fraction of the cell is prepared according to the method of Haurand and Ullrich et al.[J. Biol. Chem. 260, 15059–15067 (1985)]. The obtained cells ($2 \times 10^8$ cells) are homogenized in a solution (20 ml) of 10 mM potassium phosphate buffer (pH 7.0), 10 mM EDTA, 5 mM glucose, 0.1 mM dithiothreitol (DTT), 1.15% KCl, 2 μg/ml leupeptin, 2 μg/ml pepstatin, 10 μg/ml soybean trypsin inhibitor and 44 μg/ml phenylmethylsulfonyl fluoride, and subjected to ultrasonication (30 seconds, 4 times) using a Branson sonifier model 450.

The obtained homogenate is centrifuged at 7,000×g for 15 minutes, and the obtained supernatant is centrifuged at 105,000×g for 60 minutes. The sediment obtained is suspended in 10 mM potassium phosphate buffer (3 ml, pH 7.0) containing 20% glycerol, 1 mM DTT and 1 mM EDTA by sonication. The protein concentration is determined by Lowry method using bovine serum albumin as a standard, and a solution for immunoblot analysis and PGIS assay at 5 mg/ml is prepared.

(3) Western Immunoblot Analysis

The infected Sf9 cells and human platelet microsomal fraction are subjected to 10% SDS-PAGE according to the method of Laemmli [Nature 227, 680–685 (1979)]. The migrated protein is electrophoretically transferred onto a polyvinylidene difluoride (PVDF) membrane (Immobilon, Millipore) according to the method of Towbin et al. [Proc. Natl. Acad. Sci. USA 76,4350–4354 (1979)] Tris-HCl buffered saline (TBS) (pH 7.4) containing 10% equine serum is pretreated at room temperature for 30 minutes, and the blot membrane is incubated with polyclonal antibody against bovine PGIS in TBS containing 3% skim milk.

After washing with TBS containing 0.05% Tween 20, the membrane is incubated in TBS containing 3% skim milk at 37° C. for 30 minutes together with anti-mouse IgG equine antibody conjugated with horseradish peroxidase (manufactured by Vector Laboratories). After thorough washing with TBS containing 0.05% Tween 20, the band showing positive immunological response is detected using an immunostaining HRP kit (manufactured by Konica).

Example 3

Figure 4:
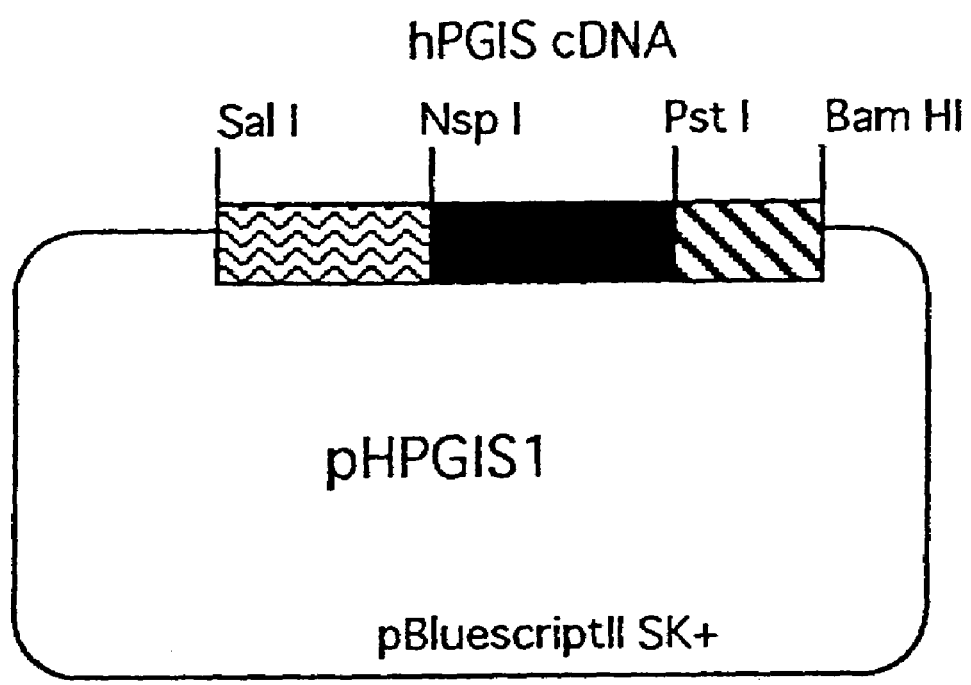
FIG. 4 shows a restriction enzyme map of plasmid pHPGIS1.

Expression of Human PGIS in Cultured Animal Cell (1) Preparation of Whole Length Human PGIS cDNA The obtained pHPGIS36 clone was cleaved out with restriction enzymes SalI and NspI and purified to give a SaLI-NspI fragment. The pHPGIS135 clone was cleaved out with restriction enzymes PstI and BamHI and purified to give a PstI-BamHI fragment. Furthermore, primers [SEQ ID NO: 16: P5 primer (676–699), SEQ ID NO: 17: P6 primer (832–855)] having sequences depicted in Sequence Listing SEQ ID NOS: 16 and 17 were synthesized based on the nucleotide sequence of λ hPGIS141. Using these primers and λ hPGIS141 as a template, a middle stream region of human PGIS cDNA was amplified by PCR method, cleaved with restriction enzymes NspI and PstI, purified and confirmed for the nucleotide sequence and used as an NspI-PstI fragment. These SalI-NspI fragment, PstI-BamHI fragment and NspI-PstI fragment were bound and introduced into the SalI-BamHI site of pBluescriptII SK+ (manufactured by STRATAGENE) previously treated with SalI-BamHI, whereby a plasmid (pHPGIS1) containing the whole length human PGIS cDNA was prepared. FIG. 4 shows the restriction enzyme map of pHPGIS 1.

(2) Construction of Human PGIS Expression Vector for Cultured Animal Cell

Figure 5:
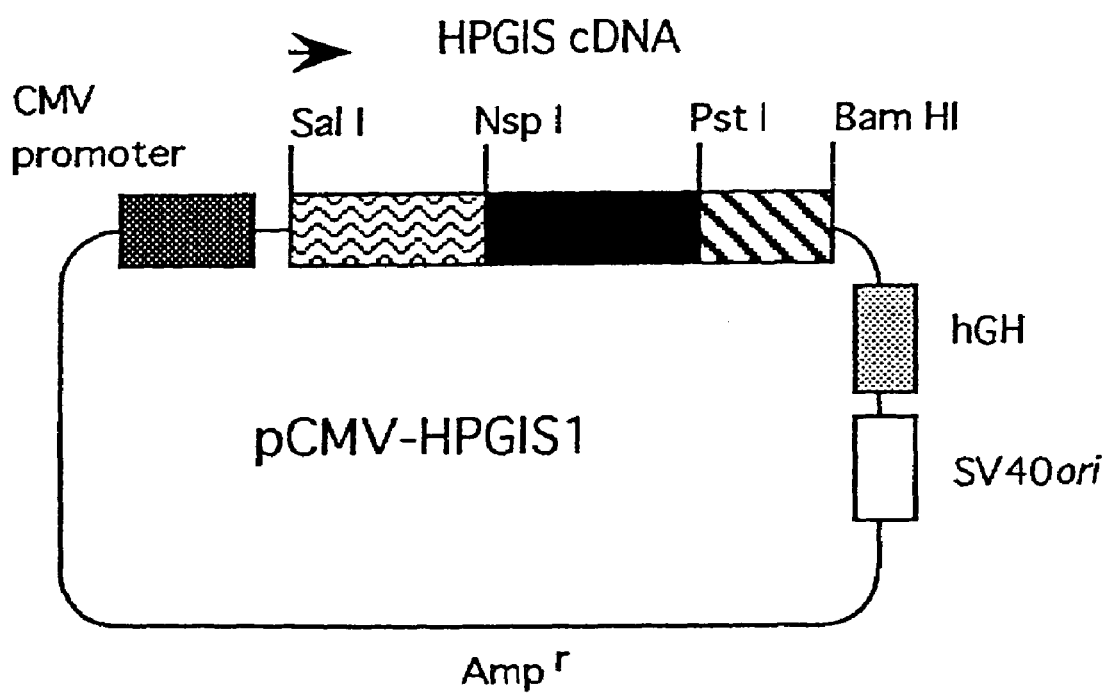
FIG. 5 shows a restriction enzyme map of human PGIS expression vector pCMV-HPGIS1.

Human PGIS cDNA insert region was cleaved out from the obtained pHPGIS1 clone with restriction enzymes SalI and BamHI and purified to give a SalI-BamHI fragment. This SalI-BamHI fragment was introduced into the SalI-BamHI site of pCMV7 expression vector [supplied by Dr. David W. Russel, University of Texas Southwestern Medical Center, Cell, 75, 187–197 (1993); J. Biol. Chem., 264, 8222–8229 (1989)] previously treated with SalI-BamHI, whereby a human PGIS expression vector (pCMV-HPGIS 1) for cultured animal cell was prepared. FIG. 5 shows the restriction enzyme map of pCMV-HPGIS 1.

(3) Expression of Human PGIS in Cultured Animal Cell

Human fetus kidney-derived 293 cells (manufactured by Dainippon Pharmaceutical Co., Ltd.) were sewn in a 60 mm dish at $3 \times 10^5$ cells, and mono-layer cultured at 37° C. for 24 hours in Dulbecco modified Eagle's medium (DMEM) containing 10% fetal calf serum, 100 U/ml penicillin and 100 µg/ml streptomycin. Then, a recombinant plasmid (pCMV-HPGIS 1, 3 µg) and pVA1 [adenovirus VA1 gene, 3 µg: supplied by Dr. David W. Russel, University of Texas Southwestern Medical Center, Mol. Cell. Biol., 7, 549–551 (1987)] were mixed and transfected by lipofectin method (GIBCO BRL). At 40 hours after the transfection, the cells were washed with phosphate-buffered saline and collected. The cells were suspended in 10 mM calcium phosphate buffer (pH 7.0) containing 10 mM EDTA, 10 mM phenylmethanesulfonyl fluoride (PMSF), 5 mM glucose, 0.1 mM dithiothreitol (DTT), 1.15% KCl, 2 µg/ml leupeptin, 2 µg/ml pepstatin and 10 µg/ml soybean trypsin inhibitor, and subjected to ultrasonication (10 seconds, 10 times) using ASTRASON™ Model XL2020.

Figure 7:
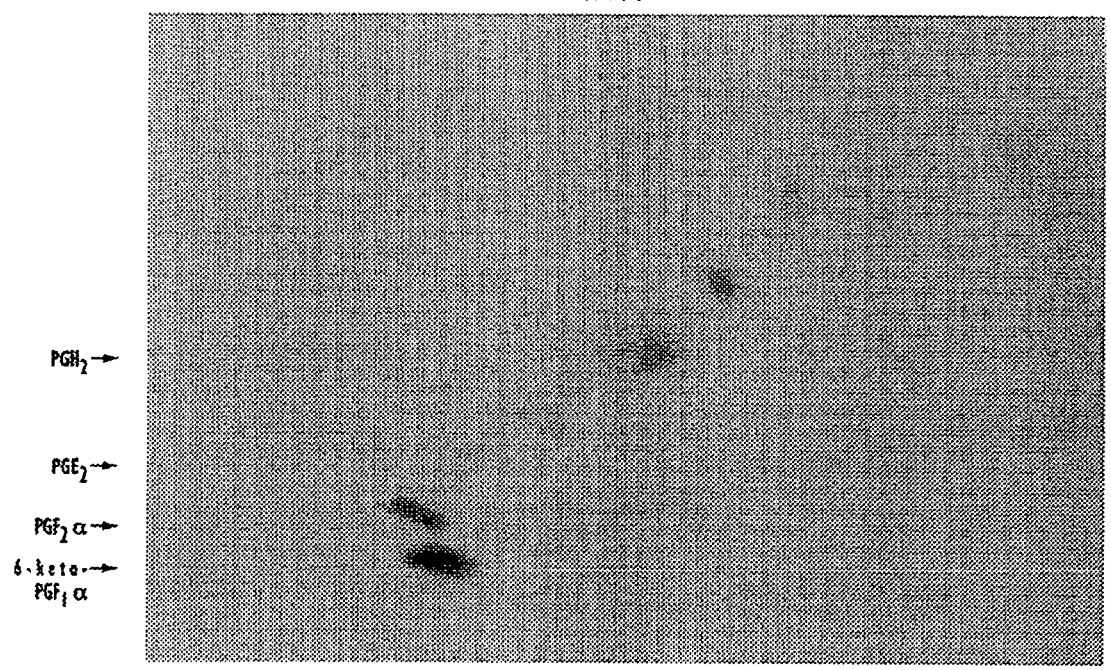
FIG. 7 is a photograph showing the results of the analysis, by thin layer chromatography, of the PGIS activity in the cells into which pCMV-HPGIS1 has been introduced.
Figure 8:
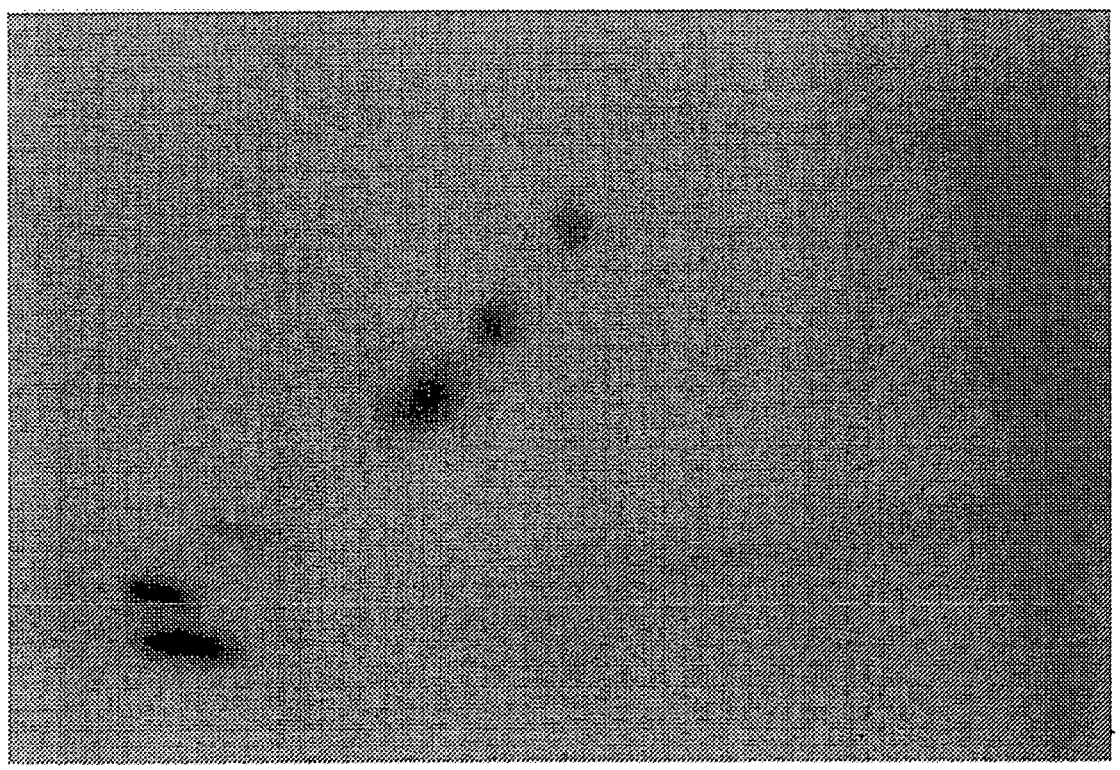
FIG. 8 is a photograph showing the results of the analysis, by thin layer chromatography, of the PGIS activity in positive control (bovine platelet microsomes).
Figure 9:
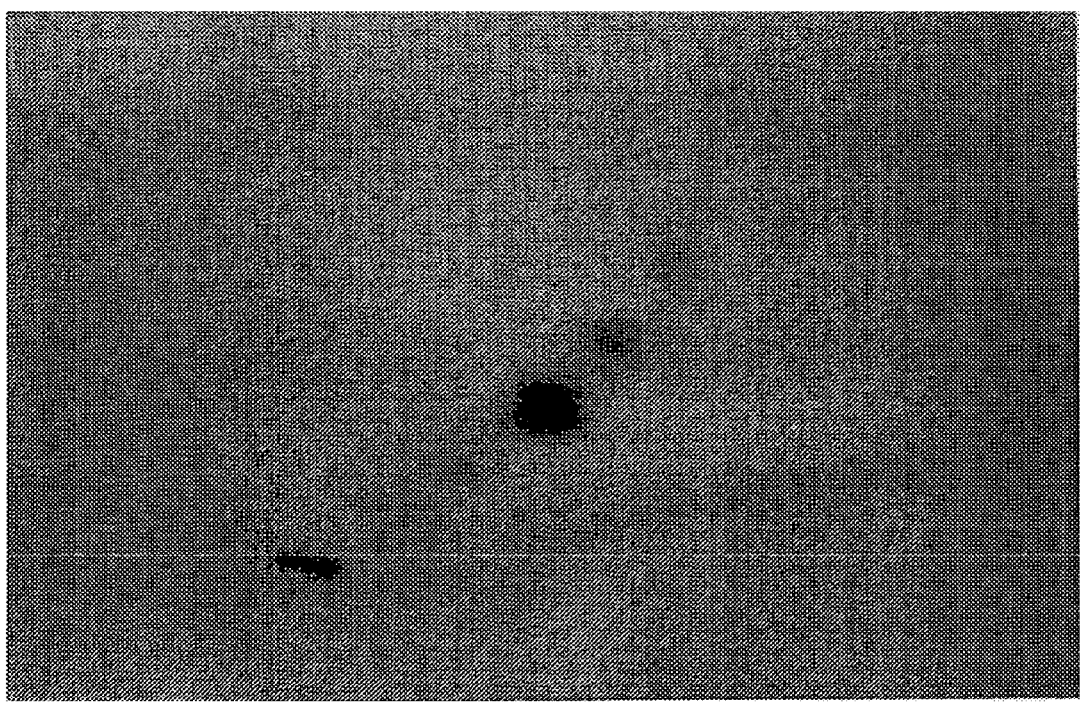
FIG. 9 is a photograph showing the results of the analysis, by thin layer chromatography, of negative control wherein pCMV alone was introduced.

The obtained homogenate was centrifuged at 100,000×g for 60 minutes and the obtained sediment was suspended in 10 mM calcium phosphate buffer (pH 7.0) containing 1 mM EDTA, 1 mM PMSF, 20% glycerol and 0.1 mM DTT. The protein concentration of the obtained sample was determined using a BCA (bicinchoninic acid) protein concentration determination kit (manufactured by PIERCE) using bovine serum albumin as a standard. The PGIS activity of the obtained sample was determined by reacting same with $^{14}C$-labeled $PGH_2$ (5 nmole) as a substrate at 24° C. for 2 minutes, separating 6-keto-$PGF_1\alpha$, which is a metabolite of the produced $PGI_2$, by thin layer chromatography, and detecting the radioactivity of the 6-keto-$PGF_1\alpha$. FIG. 7 shows the detected PGIS activity, FIG. 8 shows PGIS activity of positive control (bovine platelet microsomes) and FIG. 9 shows the analysis results, by thin layer chromatography, of negative control wherein pCMV7 alone was introduced.

As the result of the determination using a sample prepared from the cell into which an expression vector incorporating human PGIS cDNA had been introduced, a spot of 6-keto-$PGF_1\alpha$, which is a metabolite of $PGI_2$, was detected as shown by an arrow in FIG. 7. The results were the same as those obtained using bovine platelet microsome containing PGIS as a positive control (FIG. 8). In contrast, the determination using a sample prepared from the cell into which an expression vector without human PGIS cDNA had been introduced failed to detect a spot of 6-keto-$PGF_1\alpha$. The spot of $PGH_2$ was thicker (FIG. 9) than in FIG. 7 and FIG. 8. The above results mean that PGIS cDNA incorporated in the expression vector was expressed as a recombinant protein (recombinant PGIS) having PGIS activity and this protein acted on $PGH_2$ to produce 6-keto-$PGF_1\alpha$ which is a metabolite of $PGI_2$.

Example 4

Expression of Human PGIS in Cultured Animal Cell

Figure 6:
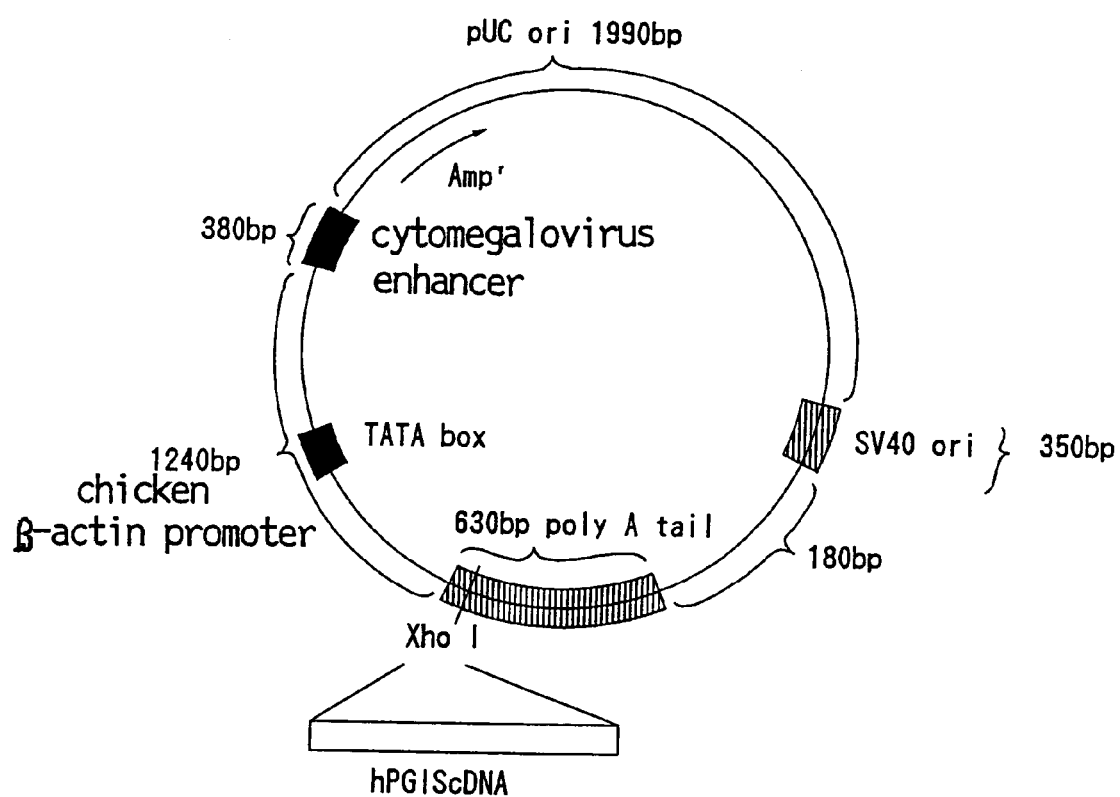
FIG. 6 shows an expression vector pUC-CAGGS.

Human PGIS cDNA was bound to the XhoI site of the expression vector pUC-CAGGS [having an enhancer of cytomegalovirus and chiken beta-actin promoter] as shown in FIG. 6 [prepared according to the description in Gene 108, 193–200 (1991)] to construct an expression vector. Two kinds of vectors, i.e., this vector and a vacant vector without human PGIS cDNA, were introduced into vascular smooth muscle cells respectively prepared from rat aorta by HVJ-liposome method [Hypertension 21, 894–899 (1993)] and incubated in a serum-free medium [Dulbecco modified Eagle's medium (DMEM) containing $5 \times 10^{-7}$ M insulin, 50 µg/ml transferin, 0.2 mM ascorbic acid, 100 U/ml penicillin and 100 µg/ml streptomycin] in a $CO_2$ incubator at 37° C. for 2 days. Then, the medium was changed to a medium containing 1% or 5% fetal calf serum (FCS), and $^3H$-thymidine was added 16 hours later. At 8 hours after the addition of thymidine, the thymidine uptake was determined by a conventional method [Cancer Immunol. Immunother. 24, 158–164 (1987)].

Figure 10:
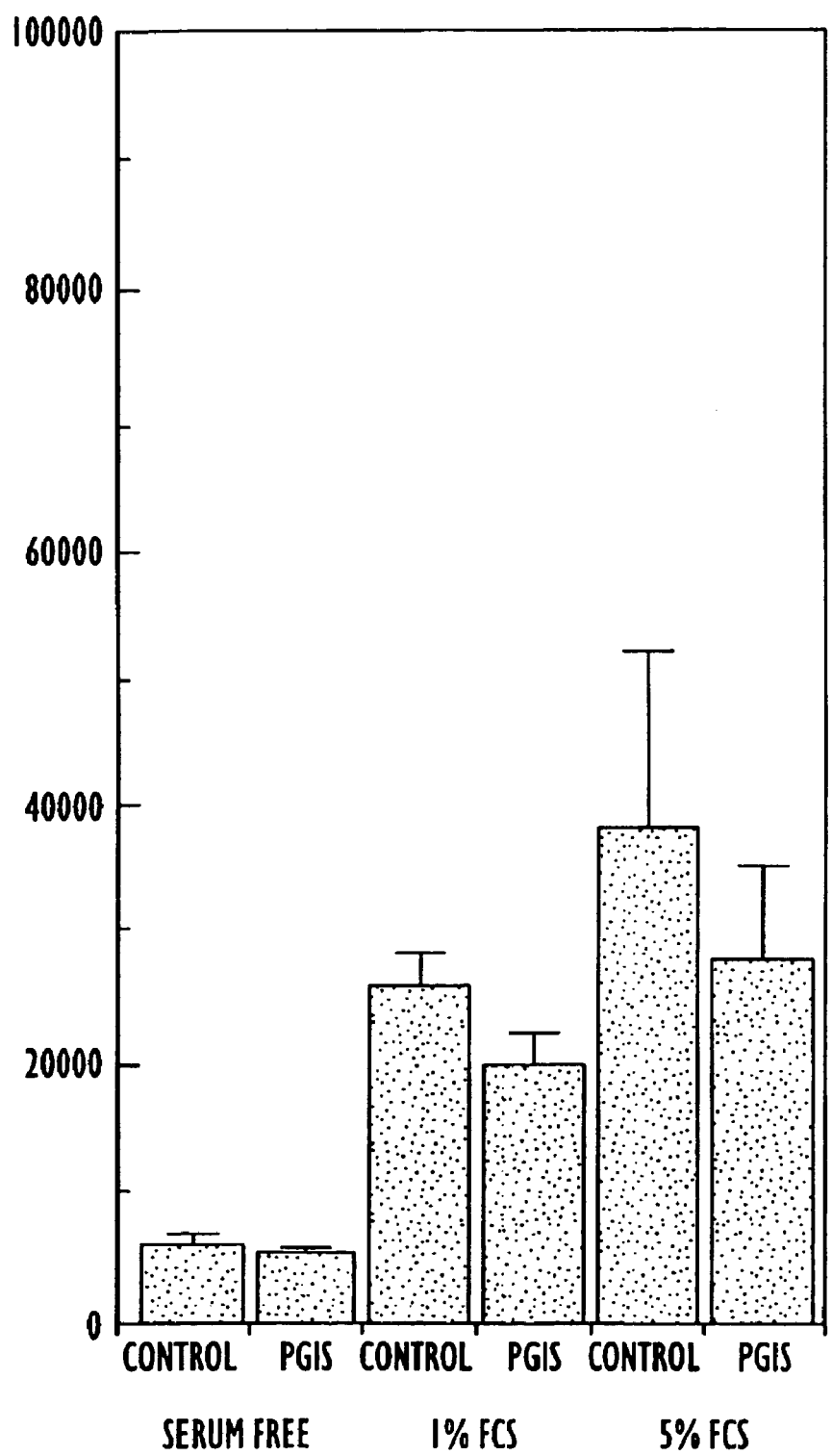
FIG. 10 is a graph showing the effects of the introduction of human PGIS expression vector on the blood vessel smooth muscle cell proliferation.

The results are shown in FIG. 10, wherein control was a cell into which a vacant vector was introduced and PGIS was a cell into which an expression vector bound with human PGIS cDNA was introduced.

Addition of serum to the vascular smooth muscle cell cultured in the absence of serum led to a promoted proliferation which increased thymidine uptake. In the vascular smooth muscle cell into which an expression vector ligated with human PGIS cDNA was introduced, thymidine intake, namely, proliferation, was significantly suppressed as compared to the cell into which a vacant vector was introduced. This result suggests the possibility of PGIS cDNA introduction suppressing abnormal growth of smooth muscle cells in vascular intima which is observed in arteriosclerosis and the like.

Example 5

Preparation of Anti-PGIS Polyclonal Antibody

PGIS dissolved in 0.5 ml of phosphate-buffered saline (PBS) and an equivalent amount of adjuvant were emulsified and subcutaneously injected to rabbit. Thereafter, similar subcutaneous injection was given twice every 10 days, and blood was taken from the rabbit 10 days after the final subcutaneous injection. Anti-PGIS/IgG was purified and obtained from rabbit anti-PGIS serum prepared from the blood of said rabbit using protein A sepharose 4B (Bio-Rad).

Example 6

Preparation of Anti-PGIS Monoclonal Antibody (1) Mouse

Male inbred line BALB/c mice (5 weeks of age) were obtained and bred on standard pellet in an animal breeding chamber (23+1° C., 70% humidity) with optional watering.

(2) Immunogen

Human-originated purified PGIS was used. The human PGIS was prepared to a concentration of 1 mg/ml with Dulbecco PBS, dispensed into test tubes by 100 μg and freeze-preserved at −80° C. until use.

(3) Immunizing Method

Human PGIS 100 μg/0.5 ml and an equivalent amount of Freund's complete adjuvant were mixed. An emulsified antigen (20 μg) was administered to five male BALB/c mice (5 weeks of age) intraperitoneally and subcutaneously at dozen sites on the back every 2 weeks for 2 months. After the immunization for 2 months, antibody titer was measured, and the mice having high antibody titer were picked and applied with additional intraperitoneal administration of 50 μg, 100 μg or 200 μg thereof every other week.

After the immunization for 2 months, two different mice were intraperitoneally administered with 100 μg thereof after a blank of one month. One week later, 100 μg thereof was intravenously injected for additional immunization.

(4) Cell Fusion

At 3 days from the final immunization, the spleen of the BALB/c mice was removed to prepare suspensions of spleen cells in EMEM culture medium. The spleen cells were washed 4 times with EMEM culture medium and counted.

For cell fusion, 2-amino-6-oxy-8 azapuraine (8-Azaguanine)-resistant BALB/c mouse myeloma-derived cultured cell line (P3-X63-Ag8.653, hereinafter abbreviated as X63 cells) was used as a parent cell line. The X63 cells were subcultured in RPMI-1640 culture medium (20 μg/ml, containing 8-Azaguanine) supplemented with 5% inactivated fetal calf serum (FCS), and X63 cells in the logarithmic growth phase were washed 3 times with RPMI-1640 culture medium and counted.

Cell fusion is performed in RPMI-1640 culture medium containing polyethylene glycol 4000 at a concentration of 50 (w/v) %.

That is, spleen cells and X63 cells are mixed at a ratio of 10:1 and centrifuged at 1500 rpm for 5 minutes. Supernatant is removed, and cell pellets are thoroughly suspended and subjected to cell fusion according to the method of Kohler and Milstein using polyethylene glycol. Thereafter, the spleen cells are suspended in an HAT selective medium (10% FCS-added RPMI-1640 culture medium containing $1\times10^{-4}$ M hypoxanthine, $4\times10^{-7}$ M aminopterin and $1.6\times10^{-5}$ M thymidine) so that the spleen cells are contained at a concentration of $3.5\times10^6$ cells/ml. Then, the cell suspension is dispensed into each well of 96 well microtest plate by 100 μl and cultured in a carbonic acid gas incubator (37° C., 95% humidity, 8% carbonic acid gas). On day 1 and day 2 after the initiation of culture, HAT medium is added by one drop to each well and by 2 drops on day 7 and day 9 after the initiation of incubation, which is followed by further culture.

(5) Screening

From 10 days after the initiation of culture, clone cells emerge. For confirmation of antibody production, hybridoma culture supernatant is subjected to an antigen-antibody reaction test.

That is, 50 μl each from hybridoma culture supernatant and human PGIS antigen liquid is placed in a U-bottomed microtiter plate and thereto is added 50 μl of 20% suspension of Sepharose 4B bound with anti-mouse immunoglobulin antibody. The mixture is stirred at room temperature for one hour and left standing for 10 minutes. After confirmation of complete sedimentation of anti-mouse immunoglobulin antibody-bound Sepharose 4B on the bottom of the well, 20 μl of the supernatant is taken and determined for concentration of residual human PGIS in the supernatant by PGIS ELISA system. When anti-human PGIS monoclonal antibody against human PGIS is present in the hybridoma culture supernatant, human PGIS and anti-human PGIS monoclonal antibody react and anti-mouse immunoglobulin antibody-bound Sepharose 4B sediment is formed as an antigen-antibody complex to decrease the concentration of residual human PGIS in the supernatant, thus proving the presence of anti-human PGIS monoclonal antibody.

Example 7

A synthetic peptide (with 14 residues), GCGIEAL-PRTHESQ (SEQ ID NO: 20) corresponding to amino acid residues 182–193 of human PGIS, fused to Gly-Cys at the N-terminus, was coupled to keyhole limpet hemocyanin (KLH) by standard method. Thus, the peptide itself is GIEALPRTHESQ (SEQ ID NO: 18). The corresponding sequence for bovine PGIS is GVEAPPHTQESQ (SEQ ID NO: 19). A Japanese white rabbit was injected with 700 μg of the conugated peptide in Freund's complete adjuvant subcutaneously, and was boosted every 2 weeks, 3 times (700 μg of the conjugate in Freund's incomplete adjuvant). After one week from the third boost, the blood was collected from the rabbit carotid artery and the serum was used for immunoblotting as antiserum against human PGIS.

The human and bovine PGIS were prepared using the BAC- to BACTM Baculovirus Expression System (Invitrogen). The entire protein coding region of human or bovine cDNA was inserted into the pFastBac-1 donor plasmid. The constructed plasmids were transfected into DH10Bac competent cells, and the recombinant bacmid DNAs and the recombinant baculovirus generated according to the manufacture's instruction. The recombinant baculovirus or empty (Mock) baculovirus were infected to *Spodoptera frugiperda* 21 (Sf21) insect cells and the cells were cultured at 27° C. in Grace's insect cell culture medium supplemented with 10% fetal bovine serum, 0.4% yeastolate, 0.4% lactalbumin hydrolysate and 5 mg/ml hematin. After 72 h, the cells were harvested and solubilized microsome was prepared according to J. Biol. Chem., 1994, 269(31):19897–19903. Solubilized microsome proteins (2 μg/lane) were separated by 10% SDS-polyacrylamide gel electrophoresis according to the method of Laemmli. For immunoblotting analysis, proteins were transferred electrophoretically onto a polyvinylidene fluoride membrane (Millipore) for 1.5 h at 1.5 mA/cm². The membrane was blocked with 5% skim-milk in 20 mM Tris-HCl, pH 7.5 containing 500 mM NaCl and 0.05% Tween 20 (Tris-buffered salt solution with Tween 20, TBS-T) at room temperature overnight. Subsequently, the membrane was blocked with 1% BSA in TBS-T at room temperature for 1 h and then incubated with the antiserum (×200) against human PGIS for 1 h. After the membrane was rinsed with TBS-T 3 times for 10 min, it was incubated with horseradish peroxidase conjugated anti-rabbit IgG (×1000, Daco) in TBS-T containing 1% BSA for 1 h. After washing with TBS-T 4 times for 10 min., the membrane was reacted with the ECL detection reagents (Amersham Pharmacia Biotech Ltd.) and exposed to X-ray film. For stripping antibodies from the membrane, the membrane was washed with 62.5 mM Tris-HCl 6.7 containing 2% SDS and 0.1 M 2-mercaptoethanol at 50° C. for 30 min and then in TBS-T at room temperature twice for 10 min. After blocking, the membrane was reacted with the polyclonal antiserum (×1000) against murine PGIS (whole) and the secondary antibody, and then the signal was detected as described above. The results are shown in FIG. 14.

Figure 14:
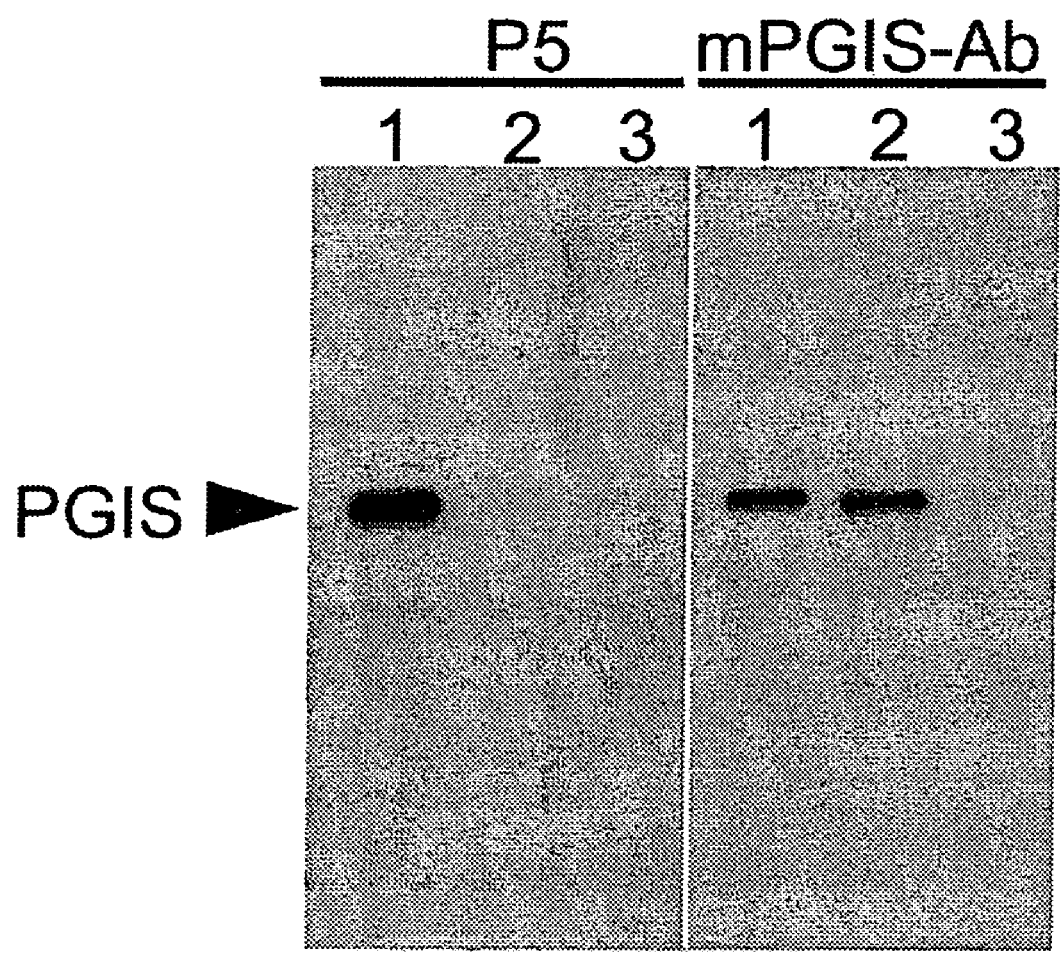
FIG. 14 depicts a Western blot analysis of Example 7.

FIG. 14 displays the detected signals on the membrane reacted with the antiserum against human (left panel) or murine (right panel) PGIS. Lane 1, human PGIS-infected Sf21 cells; lane 2, bovine PGIS-infected Sf21 cells, lane 3, Mock-infected Sf21 cells.

From the above experiment, it was found that antiserum against human PGIS reacted with human PGIS, but did not react with bovine PGIS. On the other hand, antiserum against murine PGIS cross-reacted with both human and bovine PGIS. These results clearly demonstrate that the inventive antibody is highly specific to human PGIS.

The human "synthetic" peptide used in this Example 7 is SEQ ID NO: 18 and the corresponding bovine PGIS sequence is SEQ ID NO: 19, differing from the human PGIS sequence at four amino acid locations.

Example 8

Purification of Anti-PIS Polyclonal Antibody

The anti-PGIS polyclonal antibody, prepared in Example 7, is purified by well known techniques, such as ammonium sulfate precipitation, gel filtration chromatography, ion exchange chromatography or affinity chromatography using protein A or protein G, which provide primarily the IgG fraction of immune serum. For the further purification of the crude anti-PGIS IgG fraction by affinity chromatography, the synthetic peptide with the sequence GIEALPRTHESQ is covalently immobilized on a Sepharose. Crude anti-PGIS IgG fraction is applied to the peptide-conjugated-Sepharose, and subsequently washed with PBS. The antibodies are eluted from the peptide-conjugated-Sepharose with 0.1 mol/l acetic acid (pH 2.5), and the antibody solution is neutralized with solid sodium phosphate (0.01 mol/1).

Reference Example 1

RNA Blot Analysis

RNA blot hybridization analysis was made to examine the influence of several kinds of cytokines on the expression of HAEC-derived human PGIS mRNA.

The entire RNA (30 μg) derived from each HAEC which was incubated for 24 hours with several kinds of cytokines [IL-1α (1 ng/ml), IL-1β (1 ng/ml), IL-6 (2.5 ng/ml), TNF-α (5 ng/ml) and TNF-β (1 ng/ml)] was denatured with formamide, electrophoresed on 1% agar gel containing 1.5% formaldehyde, and transferred onto a nylon membrane. A probe [pHPGIS 135 and glyceraldehyde-3-phosphate dehydrogenase (GAPDH)] was labeled with [α-$^{32}$ P]dCTP by random priming method [Feinberg, A. P., and Vogelstein, B. (1983) Anal. Biochem. 132, 6–13].

Figure 11:
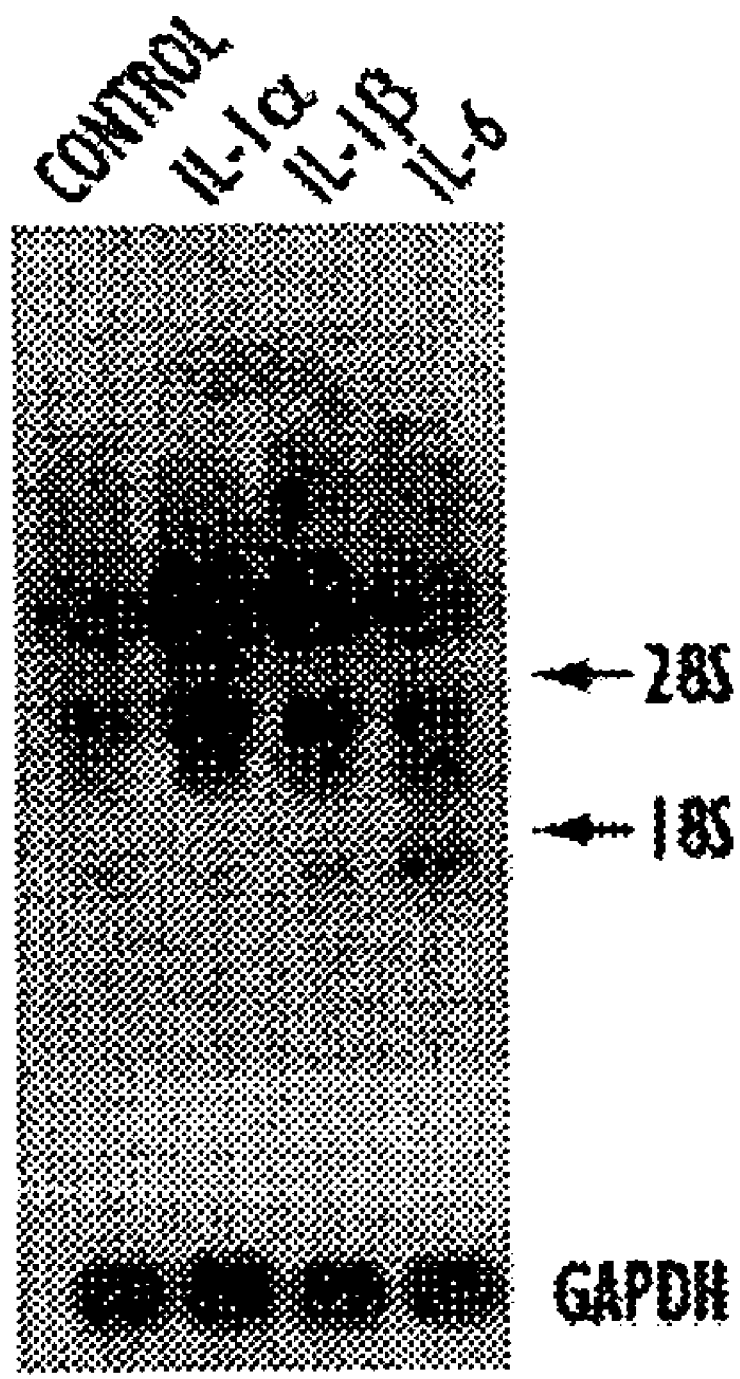
FIG. 11 is a photograph showing the results of RNA blot (electrophoresis) analysis of human PGIS mRNA treated with cytokines.

Then, hybridization was applied according to the method described in Biochem. Biophys. Res. Commun. 178, p 1479–1484 (1991). The membrane obtained was washed with 0.1× SSC (0.15M NaCl, 0.015M sodium citrate, pH 7.0) containing 0.1% SDS at 60° C., air-dried and autoradiographed. The results are shown in FIG. 11. The main band of the HAEC-derived human PGIS mRNA was found at about 6 kb and three other minor bands were found (3.2, 2.5 and 1.7 kb). The test results revealed that the expression of human PGIS mRNA incubated for 24 hours with IL-1α, IL-1β, or IL-6 increased about 2-fold as compared with the control without cytokine treatment. Accordingly, increase in $PGI_2$ production caused by cytokine is considered to be attributable to the increased expression and production of PGIS which was achieved by cytokine. Thus, the treatment with cytokine is an extremely useful method for increasing PGIS expression to increase PGIS activity, which in turn accelerates $PGI_2$ production.

Reference Example 2

In Vivo Distribution of PGIS mRNA

RNA blot analysis was made to examine the distribution of PGIS mRNA expression in human body. Specifically, a filter was purchased from Clone-Tech on which poly (A)$^+$ RNA of various human tissues was electrophoresed and blotted. hPGIS135 was labeled with $^{32}$P by the aforementioned method and subjected to Northern blot hybridization under the same conditions as above.

Figure 12:
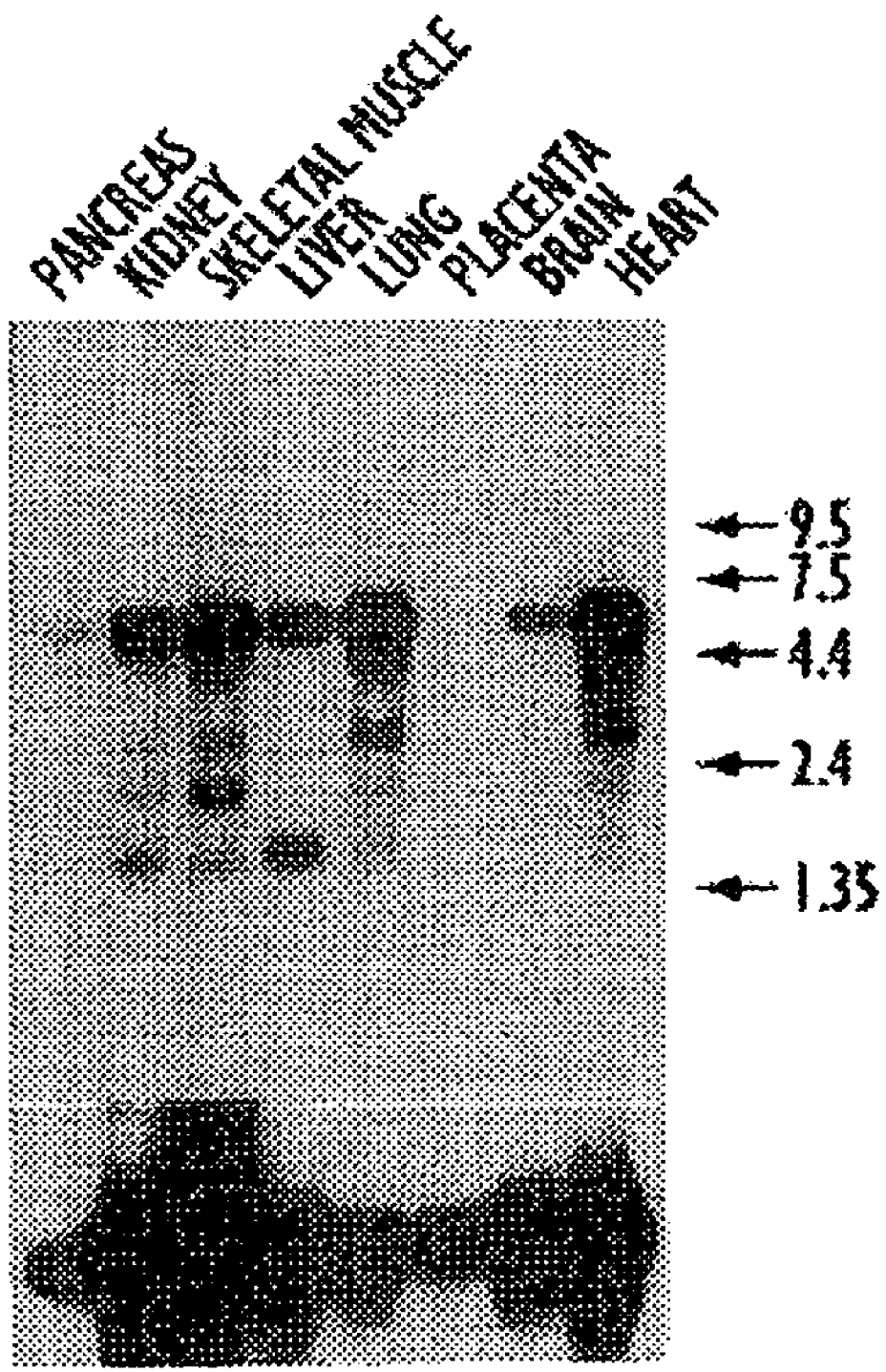
FIG. 12 is a photograph showing the distribution of PGIS mRNA expression in human body (pancreas, kidney, skeletal muscle, liver, lung, placenta, brain and heart) by electrophoresis.
Figure 13:
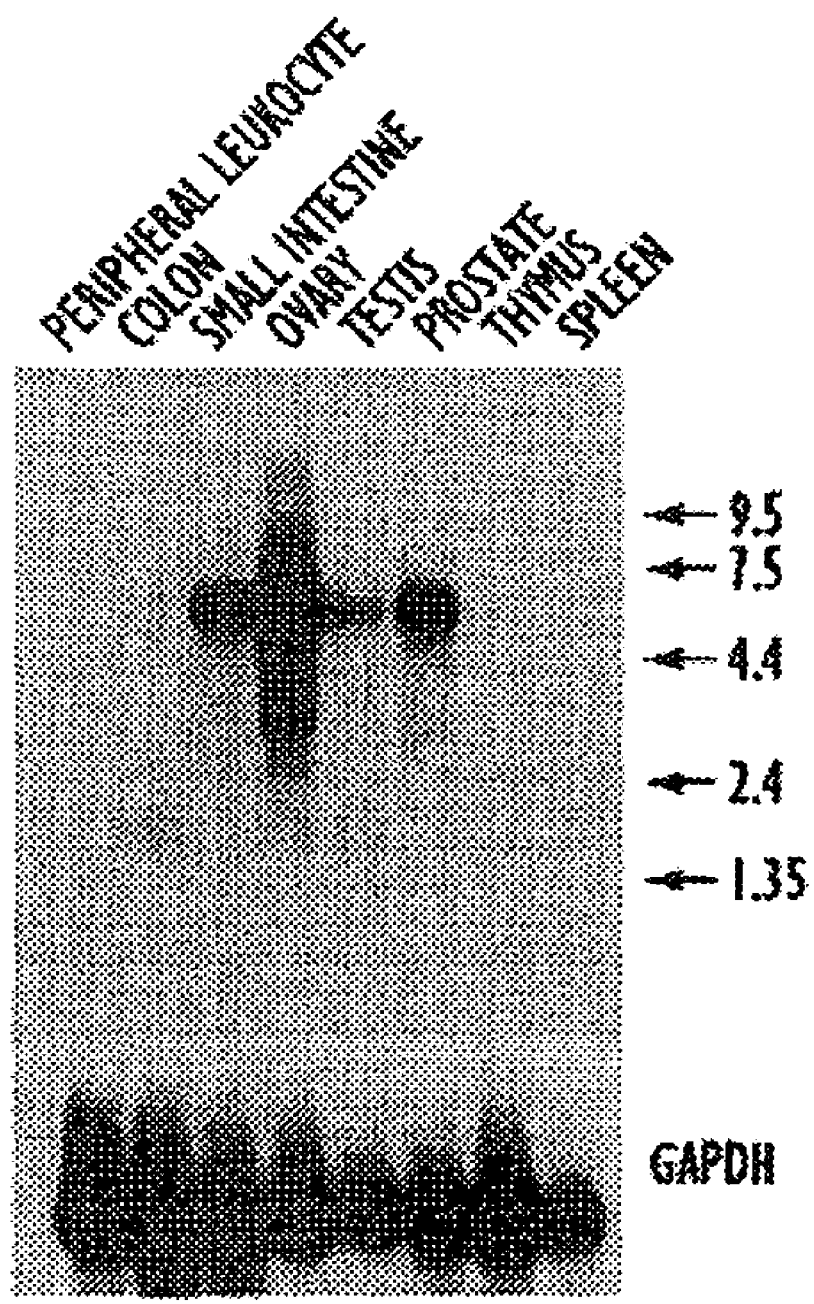
FIG. 13 is a photograph showing the distribution of PGIS mRNA expression in human body (peripheral leukocyte, large intestine, small intestine, ovary, testicle, prostate, thymus and spleen) by electrophoresis.

The results are shown in FIG. 12 and FIG. 13. The results confirm that PGIS mRNA was abundantly expressed widely in human tissues, particularly, in uterus, heart, skeletal muscle, lung and prostate and at significant levels, though slightly, in small intestine, kidney, liver and brain. These results coincide with the conventional reports of enzymatic activity and distribution in tissue of immunological response of PGIS, thus suggesting various biological roles assumed by PGIS besides the action in the vascular system. The 6 kb main, strong band and 3 weak bands as shown in FIG. 11 were observed in all tissues mentioned above, though relative thickness among the weak bands varied between tissues. Such various modes of presence of transcription products suggest possible different splicing of mRNA or the presence of an analogous gene (isozyme) as found in prostaglandin endoperoxidase.

What is claimed is:

1. An isolated or purified antibody that specifically binds an amino acid sequence consisting of residues 1–12 of SEQ ID NO:18.

2. The antibody according to claim 1, wherein said antibody is a monoclonal antibody.

3. The antibody according to claim 2, wherein said antibody is a purified IgG fraction.

4. The antibody according to claim 1, wherein said antibody is a polyclonal antibody.

5. The antibody according to claim 1, wherein said antibody specifically binds to a polypeptide as set forth in SEQ ID NO:15 or SEQ ID NO:20.

6. The antibody according to claim 5, wherein said antibody is a monoclonal antibody.

7. The antibody according to claim 6, wherein said antibody is a purified IgG fraction.

8. The antibody according to claim 5, wherein said antibody is a polyclonal antibody.

9. The antibody according to claim 1, wherein said antibody binds to human prostacyclin synthase, shown in SEQ ID NO:15, and does not bind to bovine prostacyclin synthase.

10. An isolated or purified antibody that specifically binds an amino acid sequence consisting of residues 1–12 of SEQ ID NO:18, said antibody produced using an immunogen comprising a polypeptide, wherein said polypeptide comprises residues 1–12 of SEQ ID NO:18.

11. The antibody of claim 10, wherein said polypeptide consists of residues 1–12 of SEQ ID NO:18.

12. The antibody of claim 10, wherein said immunogen further comprises complete Freund's adjuvant or keyhole limpet hemocyanin.

13. A method for producing an antibody that specifically binds an amino acid sequence consisting of residues 1–12 of SEQ ID NO:18, comprising;
  (a) administering an immunogen comprising a polypeptide to an animal, wherein said polypeptide comprises residues 1–12 of SEQ ID NO:18, and
  (b) isolating an antibody from said animal of (a) that specifically binds an amino acid sequence consisting of residues 1–12 of SEQ ID NO:18.

14. The method according to claim 13, wherein said polypeptide consists of residues 1–12 of SEQ ID NO:18.

15. The method according to claim 13, wherein said immunogen further comprises complete Freund's adjuvant or keyhole limpet hemocyanin.

16. The method according to claim 13, wherein said antibody has the following properties (A) and (B):
  (A) specifically binds human prostacyclin synthase, shown in SEQ ID NO:15, and
  (B) does not bind bovine prostacyclin synthase.

* * * * *